(12) United States Patent
Kiyosue et al.

(10) Patent No.: US 7,951,930 B2
(45) Date of Patent: May 31, 2011

(54) **CULTURED *XENOPUS LAEVIS* CELL LINES EXPRESSING MUTANT *ADENOMATOUS POLYPOSIS COLI* GENE**

(75) Inventors: Yuko Kiyosue, Kyoto (JP); Hiroyuki Sasaki, Yokohama (JP); Shoichiro Tsukita, Kyoto (JP)

(73) Assignee: Eisai R&D Management Co., Ltd., Tokyo (JP)

(*) Notice: Subject to any disclaimer, the term of this patent is extended or adjusted under 35 U.S.C. 154(b) by 526 days.

(21) Appl. No.: 12/053,198

(22) Filed: Mar. 21, 2008

(65) Prior Publication Data

US 2010/0003747 A1    Jan. 7, 2010

Related U.S. Application Data

(62) Division of application No. 10/525,621, filed as application No. PCT/JP03/10434 on Aug. 19, 2003, now Pat. No. 7,371,843.

(30) Foreign Application Priority Data

Aug. 22, 2002 (JP) ................. 2002-241487

(51) Int. Cl.
   *C07H 21/04* (2006.01)
   *C07H 21/02* (2006.01)
   *C12N 15/00* (2006.01)
   *C12N 5/00* (2006.01)

(52) U.S. Cl. .............. 536/23.5; 435/320.1; 435/325; 536/23.1

(58) Field of Classification Search .............. None
See application file for complete search history.

(56) References Cited

FOREIGN PATENT DOCUMENTS

WO    WO 01/16167 A2    3/2001
WO    WO 01/16167 A3    3/2001

OTHER PUBLICATIONS

Morin, Patrice J. et al.; "Activation of β-catenin-tcf signaling in colon cancer by mutation in β-catenin or APC"; *Science* 275:1787-1790 (Mar. 21, 1997).
Munemitsu, Susan et al.; "Regulation of intracellular β-catenin levels by the adenomatous polyposis coli (APC) tumor suppressor protein"; *Proc. Natl. Acad. Sci. U.S.A.* 92:3046-3050 (Mar. 1995).
Rubinfeld, Bonnee et al.; "Loss of β-catenin regulation by the APC tumor suppressor protein correlates with loss of structure due to common somatic mutations of the gene"; *Cancer Research* 57:4624-4630 (Oct. 15, 1997).
Spirio, Lisa et al.; "Alleles of the *APC* Gene: An attenuated form of familial polyposis"; *Cell* 75:951-957 (Dec. 3, 1993).
Bienz, Mariann; "The subcellular destinations of APC proteins"; *Nat. Rev. Mol. Cell Biol.*; May 2002; pp. 328-338; vol. 3, No. 5.
Etienne-Manneville, Sandrine and Alan Hall; "Cdc42 regulates GSK-3β and adenomatous polyposis coli to control cell polarity"; *Nature*; Feb. 13, 2003; pp. 753-756; vol. 421; Nature Publishing Group.
Fearnhead, Nicola S. et al.; "The ABC of APC"; *Human Molecular Genetics*; 2001; pp. 721-733; vol. 10, No. 7; Oxford University Press.
Fodde, Riccardo and Ron Smits; "Disease Model: familial adenomatous polyposis"; *TRENDS in Molecular Medicine*; Aug. 2001; pp. 369-373; vol. 7, No. 8.
Fodde, Riccardo et al.; "*APC*, signal transduction and genetic instability in colorectal cancer"; *Nat. Rev. Cancer*; Oct. 2001; pp. 55-67; vol. 1.
Hamada, Fumihiko and Mariann Bienz; "A *Drosophila* APC tumour suppressor homologue functions in cellular adhesion"; *Nature Cell Biology*; Mar. 2002; pp. 208-213; vol. 4.
Jimbo, Takeshi et al.; "Identification of a link between the tumour suppressor APC and the kinesin superfamily"; *Nature Cell Biology*; Apr. 2002; pp. 323-327; vol. 4.
Joslyn, Geoff et al.; "Dimer formation by an N-terminal coiled coil in the APC protein"; *Proc. Natl. Acad. Sci. U.S.A.*; Dec. 1993; pp. 11109-11113; vol. 90.
Juwana, Jan-Peter et al.; "*EB/RP* gene family encodes tubulin binding proteins"; *Int. J. Cancer*; 1999; pp. 275-284; vol. 81; Wiley-Liss, Inc.
Kawasaki, Yoshihiro et al.; "Mutated APC and Asef are involved in the migration of colorectal tumour cells"; *Nature Cell Biology*; Mar. 2003; pp. 211-215; vol. 5.
Kawasaki, Yoshihiro et al.; "Asef, a link between the tumor suppressor APC and G-protein signaling"; *Science*; Aug. 18, 2000; pp. 1194-1197; vol. 289.
Kielman, Menno F. et al.; "*Apc* modulates embryonic stem-cell differentiation by controlling the dosage of β-catenin signaling"; *Nature Genetics*; Dec. 2002; pp. 594-605; vol. 32.
Lamlum, Hanan et al.; "*APC* mutations are sufficient for the growth of early colorectal adenomas"; *Proc. Natl. Acad. Sci. U.S.A.*; Feb. 29, 2000; pp. 2225-2228; vol. 97, No. 5.
Matsumine, Akihiko et al.; "Binding of APC to the human homolog of the *Drosophila* discs large tumor suppressor protein"; *Science*; May 17, 1996; pp. 1020-1023; vol. 272.
Mimori-Kiyosue, Yuko et al.; "Adenomatous polyposis coli (APC) protein moves along microtubules and concentrates at their growing ends in epithelial cells"; *The Journal of Cell Biology*; Feb. 7, 2000; pp. 505-517; vol. 148, No. 3; The Rockefeller University Press.
Mimori-Kiyosue, Yuko and Shoichiro Tsukita; "Where is APC going?"; *The Journal of Cell Biology*; Sep. 17, 2001; pp. 1105-1109; vol. 154, No. 6; The Rockefeller University Press.
Morin, Patrice J. et al.; "Apoptosis and *APC* in colorectal tumorigenesis"; *Proc. Natl. Acad. Sci. U.S.A.*; Jul. 1996; pp. 7950-7954; vol. 93.
Oshima, Hiroko et al.; "Morphological and molecular processes of polyp formation in $Apc^{\Delta 716}$ knockout mice"; *Cancer Research*; May 1, 1997; pp. 1644-1649; vol. 57.

(Continued)

*Primary Examiner* — Shulamith H Shafer
(74) *Attorney, Agent, or Firm* — Kilpatrick Townsend & Stockton LLP

(57) ABSTRACT

Using protein visualization techniques, cell lines stably expressing GFP-fused full-length and mutant APCs were obtained from cultured *Xenopus laevis* renal epithelial A6 cells. The use of these cells showed that mutant APCs, whose C-terminal region is absent, induced piling up of cells. Furthermore, piled up cells from mutant APC-expressing cell lines were proven to maintain the intercellular adhesive structure, representing a phenomenon similar to polyp formation in individual organisms (mice).

8 Claims, 7 Drawing Sheets

OTHER PUBLICATIONS

Oshima, Masanobu et al.; "Loss of *Apc* heterozygosity and abnormal tissue building in nascent intestinal polyps in mice carrying a truncated *Apc* gene"; *Proc. Natl. Acad. Sci. U.S.A.*; May 1995; pp. 4482-4486; vol. 92.

Rowan, A. J. et al.; "*APC* mutations in sporadic colorectal tumors: A mutational "hotspot" and interdependence of the two hits"; *Proc. Natl. Acad. Sci. U.S.A.*; Mar. 28, 2000; pp. 3352-3357; vol. 97, No. 7.

Rubinfeld, Bonnee et al.; "Binding of GSK3β to the APC-β-catenin complex and regulation of complex assembly"; *Science*; May 17, 1996; pp. 1023-1026; vol. 272.

Su, Li-Kuo et al.; "Association of the APC tumor supressor protein with catenins"; *Science*; Dec. 10, 1993; pp. 1734-1737; vol. 262.

Smith, K., et al., Wild type but not mutant APC associates with the microtubule cytoskeleton, Cancer Research, vol. 54. (1994), pp. 3672-3675.

Bowie et al, 1990, Science 247:1306-1310.

Wells, 1990, Biochemistry 29:8509-8517.

Ngo et al., 1994, The Protein Folding Problem and Tertiary Structure Prediction, Merz et al.. eds, Birkhauser, Boston, pp. 491-495.

Smith et al. 1994. Cancer Res. 54:3672-3675.

FIG. 4
A6
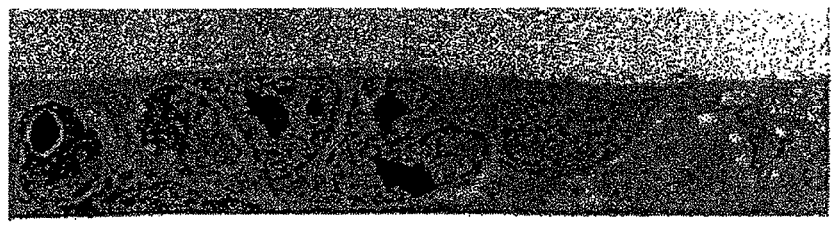
A6 / GFP-fAPC
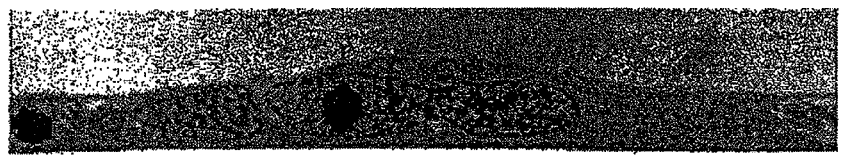
A6 / ΔcAPC-GFP
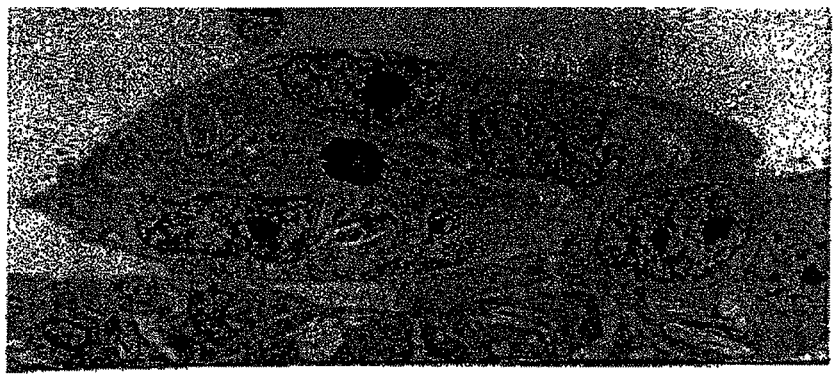
A6 / GFP-APC(ΔTSV)

CULTURED *XENOPUS LAEVIS* CELL LINES EXPRESSING MUTANT *ADENOMATOUS POLYPOSIS COLI* GENE

CROSS-REFERENCE TO RELATED APPLICATIONS

The present application is a divisional of U.S. patent application Ser. No. 10/525,621, §371(c) filed on Sep. 7, 2005, now U.S. Pat. No. 7,371,843, which is a U.S. National Stage entry of International Application No. PCT/JP2003/010434, filed Aug. 19, 2003, which claims benefit of Japanese Application No. 2002-241487, filed Aug. 22, 2002. The disclosures of each are incorporated herein by reference.

TECHNICAL FIELD

The present invention relates to mutant APC proteins that can induce piling up of cells, and to cells expressing these proteins.

BACKGROUND ART

The adenomatous polyposis coli (APC) gene is a tumor suppressor gene identified as a causative gene of Familial Adenomatous Polyposis (FAP). It has been shown that mutation of the APC gene is not restricted to FAP, but is involved also in the development of non-hereditary adenomatous polyposis and colon cancer (Polakis, P., Biochim Biophys Acta. (1997) 1332, F127-147). In FAP patients, many benign polyps form in the colon, from which malignantly transformed cancer cells develop. Although colon cancer develops through multistep changes that occur in a great number of oncogenes and tumor suppressor genes, mutations in the APC gene are found at the earliest stage. Therefore, APC gene abnormalities are considered to be causes of colon cancer.

The APC protein (hereinafter, APC) is a large protein having a molecular weight of approximately 310 kDa comprising 2843 amino acids, and binds to a great number of proteins. To date, it has been reported to bind directly to the B56 subunit of PP2A phosphatase; APC-stimulated guanine nucleotide exchange factor (Asef); KAP3/KIF3A/KIF3B microtubule-associated motor protein complex belonging to the kinesin family; β-catenin/GSK-3β/Axin, a constituent of the Wnt signal transduction pathway; microtubules, which are cytoskeleton components; proteins of the microtubule-associated protein EB/RP family; $p34^{cdc2}$ kinase, a cell cycle regulatory factor; Siah-1, an apoptosis-related protein; and hDLG, a tumor suppressor gene product (for a review, see Bienz, M., Nat. Rev. Mol. Cell Biol. (2002) 3(5), 328-338). In the polyps and colon cancer cells of FAP patients, mutations occur in both of the APC alleles, and only mutant APCs that have lost their C-terminal regions due to a truncation in the middle are expressed. Cells are thought to become cancerous because such mutant APCs exhibit abnormal functions.

APC has been reported to promote β-catenin degradation by complexing with β-catenin/GSK-3β/Axin, and to function in maintaining a low level of existing β-catenin (Rubinfeld, B., Science (1993) 262:1731-1734; Su, L. K., Science (1993) 262:1734-1737). When β-catenin is present in large amounts, it is transferred into the nucleus where it binds to a transcription factor and promotes cell proliferation. Therefore, initially, APC was considered to function as a tumor suppressor protein by regulating the level of existing β-catenin. However, detailed observation of the polyp-forming process using FAP model mice showed that epithelial cells which had differentiated in the crypt region could not migrate normally to the villus apex, and therefore dropped into the inside of the villus at the crypt-villus boundary, becoming morphologically different from their original form, resulting in polyps (Oshima, M., et al., Cancer Res. (1997 57 (9), 1644-1649). Furthermore, promotion of cell proliferation does not take place inside the polyps, and epithelial cells that develop morphologies different from the original state while maintaining an intercellular adhesive structure were proved to be the cause of polyp formation. Therefore, APC is now considered to be involved in regulating cell morphology and motility. Furthermore, APC was found to bind to Asef, which functions in the regulation of the actin cytoskeleton (Kawaki, Y., et. al. Science (2000) 289(5482), 1194-1197), and to microtubules at the leading edges of motile cells (Mimori-Kiyosue, Y. et. al., J. Cell Biol. (2000) 148(3), 505-518). The possibility of APC involvement in cytoskeleton regulation is beginning to be considered.

Elucidation of the functions of normal and mutant APCs in cell morphology and motility, and elucidation of the causes of polyp formation and malignant transformation have long been anticipated.

DISCLOSURE OF THE INVENTION

The present invention was achieved in view of the above circumstances. An objective of the present invention is to elucidate the functions of normal and mutant APCs in cell morphology and motility. Another objective of the present invention is to provide uses of the mutant APC proteins based on the obtained findings.

To elucidate APC functions in detail, the present inventors expressed full-length and truncated APCs labeled with an auto fluorescent protein (GFP; green fluorescent protein) in epithelial cells. When the fusion protein cDNAs were introduced into cells, and several strains from each independent clone stably expressing the fusion proteins were isolated by drug resistance, protruding cell layers were observed as a common feature among each of the clones that express the truncated structurally-different APCs. Observation under electron microscope showed that intercellular adhesive structures (AJ, TJ) are formed, but cell adhesion attenuates due to increased intercellular space and cell-substrate space, and the cells are piled up. In cell lines expressing full-length APC, piling up of cells did not occur and cell adhesion was strengthened. Maintenance of the intercellular adhesive structures in the cluster of piled up cells was confirmed by immunohistostaining. These results showed that mutant APCs cause piling up of cells, leading to the completion of this invention. The present inventors discovered, for the first time, the phenomenon that mutant APC-expressing cells cause piling up of cells while maintaining intercellular adhesive structures.

The mutant APCs of this invention inhibit the monolayering of normal epithelial cells, and cause the cells to pile up while maintaining cell-cell adhesion. Therefore, cells that express the mutant APCs of this invention are useful as model cells for the polyp-forming phenomenon. Furthermore, the mutant APC-expressing cells of this invention can be used to screen compounds that inhibit piling up of cells.

That is, the present invention relates to mutant APC proteins that may induce piling up of cells, cells that express these proteins, and uses of these cells. More specifically, the present invention relates to:

(1) a mutant APC protein comprising the function of inducing piling up of cells;

(2) the mutant APC protein of (1), wherein at least any one of the amino acid regions of (a) to (c) is deleted:

(a) C-terminal amino acid region starting from amino acid position 2827 in the APC protein of SEQ ID NO: 1;

(b) C-terminal amino acid region starting from amino acid position 2159 in the APC protein of SEQ ID NO: 1; and (c) C-terminal amino acid region starting from amino acid position 860 in the APC protein of SEQ ID NO: 1;

(3) the mutant APC protein of (1) or (2), wherein the protein is derived from *Xenopus laevis;*

(4) a mutant APC protein which can induce piling up of cells, wherein said protein comprises the amino acid sequence of a mutant APC protein of any one of (1) to (3), in which one or more amino acids are substituted, deleted, added, and/or inserted;

(5) a polynucleotide that encodes a mutant APC protein of any one of (1) to (4);

(6) a vector that comprises the polynucleotide of (5);

(7) a cell that comprises an artificially expressed mutant APC protein of any one of (1) to (4), or the vector of (6);

(8) the cell of (7), which is derived from a mammal;

(9) the cell of (7), which is derived from *Xenopus laevis;*

(10) a cell of any one of (7) to (9), which is an established cell line;

(11) a method of screening for a candidate compound that inhibits piling up of cells, wherein the method comprises the steps of:

(a) contacting a cell of any one of (7) to (9) with a test compound;

(b) detecting piling up of said cells; and (c) selecting compounds that inhibit the piling up of cells; and, (12) a method of screening for a polynucleotide that encodes a mutant APC protein which can induce piling up of cells, wherein the method comprises the steps of:

(a) introducing *Xenopus laevis*-derived cells with a test polynucleotide to express a mutant APC protein;

(b) culturing said cells;

(c) detecting piling up of said cells; and (d) selecting polynucleotides that pile up said cells.

The present invention provides mutant APC proteins (which are abbreviated as "mutant APCs" in parts of this specification). Expression of the mutant APCs of this invention in cells induces piling up of cells. The mutant APCs of this invention were identified by the present inventors as proteins that induce piling up of cells while maintaining cell-cell adhesion.

In the present invention, the term "mutant" refers to a protein comprising the amino acid sequence of a normal APC protein, in which one or more amino acids have been substituted, deleted, added, or inserted. Furthermore, the "mutation" may be a conservative mutation in which the amino acid used for the substitution has structural or chemical characteristics similar to those of the substituted amino acid, or a mutation involving non-conservative substitution. That is, the types of mutations present in the mutant APCs of this invention are not particularly limited, as long as they have the function of inducing piling up of cells. The mutant APCs of the present invention are usually produced artificially (or by modifying normal APCs), or obtained by isolation and purification.

APC proteins have so far been discovered in a variety of organisms. The amino acid sequences of these normal APC proteins can be obtained easily from public databases. For example, the GenBank accession numbers for the amino acid sequences of human APC protein and *Xenopus laevis* APC protein are M74088 and U64442, respectively. The amino acid sequence of *Xenopus laevis* APC protein is shown in SEQ ID NO: 1.

The mutant APCs of this invention are not limited to specific types of APC mutants. An example of the mutant APCs of this invention is a mutant of the *Xenopus laevis* APC protein comprising the amino acid sequence of SEQ ID NO: 1.

In a preferred embodiment of the present invention, the mutant APCs are proteins in which a portion of the amino acid region of a normal APC has been deleted (truncated APC proteins).

The mutant APCs of this invention are normally proteins in which the three amino acids of a TSV sequence (DLG-binding region) at the C-terminus are deleted. This TSV sequence is recognized as a PDZ protein binding motif, and binding of the hDLG protein, which is one of the PDZ proteins, is reported to occur in this region (Matsumine, A., et al., Science (1996);272(5264):1020-3). Furthermore, the mutant APCs of this invention preferably comprise an N-terminal amino acid region containing at least a "heptad repeat" and "armadillo repeat", but the mutant APCs of this invention are not limited to those containing these repeats.

More specifically, examples of the mutant APCs of this invention are proteins having a structure in which at least one of the following amino acid regions of (a) to (c) is deleted:

(a) C-terminal TSV sequence (DLG-binding region), or more specifically, the C-terminal amino acid region starting from amino acid position 2827 in the APC protein of SEQ ID NO: 1;

(b) C-terminal basic region and TSV sequence, or more specifically, the C-terminal amino acid region starting from amino acid position 2159 in the APC protein of SEQ ID NO: 1; and (c) a 15 amino-acid repeat, 20 amino-acid repeat, and C-terminal basic region and TSV sequence, or more specifically, the C-terminal amino acid region starting from amino acid position 860 in the APC protein of SEQ ID NO: 1.

The present invention also comprises proteins that have the function of inducing piling up of cells, and comprise the amino acid sequences of the above-mentioned proteins, in which one or more amino acids are deleted, substituted, or added. Methods for preparing these proteins include methods that use hybridization techniques or gene amplification techniques. More specifically, one skilled in the art can use hybridization techniques (Current Protocols in Molecular Biology edit. Ausubel et al. (1987) Publish. John Wily & Sons Section 6.3-6.4) to isolate DNAs that are highly homologous to mutant APCs, based on the DNA sequences encoding the above mutant APCs, or a portion thereof, from DNA samples derived from an organism of the same or different species, and consequently obtain the proteins of this invention. The proteins of the present invention also comprise proteins that are encoded by DNAs hybridizing with the DNAs encoding the thus isolated proteins, and which have the function of inducing piling up of cells.

Stringent hybridization conditions of "1×SSC, 0.1% SDS, 37° C." are normally used for isolating a DNA encoding a protein that comprises an amino acid sequence of mutant a APC in which one or more amino acids are deleted, substituted, or added. More stringent conditions are "0.5×SSC, 0.1% SDS, 42° C.", and even more stringent conditions are "0.2×SSC, 0.1% SDS, 65° C.". As the hybridization conditions become more stringent, isolation of DNAs having high homology to the probe sequence can be expected. However, the above combinations of SSC, SDS, and temperature conditions are only examples. Those skilled in the art can achieve similar stringencies as those described above by appropriately combining the above-mentioned factors or other factors that determine the stringency of hybridization (for example, probe concentration, probe length, and hybridization reaction time).

Polypeptides encoded by DNAs that are isolated using such hybridization techniques are usually highly homologous to the mutant APCs of this invention at the amino acid sequence level. Highly homologous refers to a sequence homology of at least 40% or higher, preferably 60% or higher, more preferably 80% or higher, even more preferably 90% or higher, still more preferably 95% or higher, and yet more preferably 97% or higher (for example, 98-99%).

The degree of homology of one amino acid sequence to another can be determined by following, for example, the BLAST algorithm by Karlin and Altschl (Proc. Natl. Acad. Sci. USA, 87: 2264-2268, 1990; Proc. Natl. Acad. Sci. USA, 90: 5873-5877, 1993). Programs such as BLASTX were developed based on this algorithm (Altschul et al. J. Mol. Biol. 215: 403-410, 1990). In the analysis of amino acid sequences using BLASTX, the parameters are, for example, score=50 and word length=3. When using the BLAST and Gapped BLAST programs, the default parameters for each program are used. The specific techniques of these analyses are known in the art (see the website at ncbi.nlm.nih.gov).

In the present invention, the phrase "piling up of cells" can be described, for example, by the cellular conditions (forms) described below, but are not particularly limited to these conditions since an exact definition is usually difficult.
(a) A height-wise overlapping of multiple nuclei from different cells is observed.
(b) Cell bodies do not dissociate from the cell layer, and exist at a position that is clearly higher than the average height (2-4 µm) of monolayered cells (for example, A6 cells).
(c) regions where cell bodies and cell nuclei are observed at the electron microscope level to be present in multiples and in a height-wise manner, are observed to have closely-winding "wrinkles" in the cellular monolayer at the light microscope level (phase contrast microscopy).

In the present invention, one skilled in the art can determine whether a protein can induce piling up of cells using known methods. For example, whether cells expressing a target protein are piled up can be confirmed readily by phase contrast microscopy or fluorescent antibody methods.

Those skilled in the art can produce mutant APCs of this invention by commonly known methods (PCR and such), for example, by using the nucleotide sequence of a DNA encoding a normal APC protein as a template. For example, the above mutant APC proteins can be produced by PCR amplification of the DNAs that encode these proteins, using the cDNA or genomic DNA of normal APCs as templates, and by cloning these DNAs into expression vectors. The cDNAs of normal APCs can be obtained by those skilled in the art by known methods, for example, by constructing a cDNA library from cells expressing normal APCs, and then performing a hybridization using a portion of the APC cDNA as a probe. The cDNA library may be prepared, for example, by a method described in literature (Sambrook, J. et al., Molecular Cloning, Cold Spring Harbor Laboratory Press (1989)), or a commercially available DNA library may also be used.

More specifically, the above mutant APCs may be produced by methods presented in the Examples below. Those skilled in the art can appropriately modify methods shown in the Examples below to produce mutant APCs to carry any amino acid region of a normal APC.

Furthermore, a mutant APC of this invention can be produced by modifying the amino acid sequence of a normal APC protein (for example, the amino acid sequence of SEQ ID NO: 1). For example, an amino acid sequence can be modified by modifying the nucleotide sequence of a DNA encoding a normal APC protein, using well-known methods such as site-directed mutagenesis (Current Protocols in Molecular Biology edit. Ausubel et al. (1987) Publish. John Wily & Sons Section 8.1-8.5), and expressing the DNA with a modified nucleotide sequence in an appropriate cell. Since amino acid mutations in proteins may occur in a natural environment (in nature), the proteins of this invention include isolated natural mutant APC proteins as long as they comprise the function of inducing piling up of cells while maintaining cell-cell adhesion, although the mutant APCs of this invention are normally produced artificially.

The mutant APCs of the present invention can be prepared as recombinant polypeptides by methods well known to those skilled in the art. A recombinant polypeptide can be prepared, for example, by inserting a DNA encoding a mutant APC of this invention into an appropriate expression vector, collecting a transformant obtained by transfecting the vector into an appropriate host cell, and purifying the polypeptide after obtaining an extract by chromatography such as ion exchange chromatography, reverse phase chromatography, gel filtration chromatography, or affinity chromatography in which an antibody against the mutant of this invention is fixed onto a column, or by a combination of these columns.

Furthermore, when a mutant APC of the present invention is expressed in a host cell (for example, an animal cell or *E. coli*) as a fusion polypeptide with a glutathione S-transferase protein or recombinant polypeptide with multiple histidine residues, the expressed recombinant polypeptide can be purified using a glutathione column or a nickel column. After the fused polypeptide is purified, regions other than the desired mutant can be removed from the fused polypeptide, as necessary, by cleavage with thrombin, factor Xa, etc.

The present invention also includes polynucleotides encoding the mutant APCs of this invention. The polynucleotides comprise DNAs that encode the mutant APCs of this invention, and RNAs which are transcription products of these DNAs.

Furthermore, the present invention provides vectors into which DNAs of the present invention are inserted. The vectors of the present invention are useful in expressing or producing the mutant APCs of the present invention in cells.

When *E. coli* is used as a host cell, there is no particular limitation other than that the above-mentioned vector should have an "ori" and a marker gene. The "ori" is used to amplify and mass-produce the vector in *E. coli* (e.g., JM109, DH5α, HB101, or XL1Blue and such). The marker gene is used to select the transformed *E. coli* (e.g., a drug-resistance gene selected by an appropriate drug such as ampicillin, tetracycline, kanamycin, or chloramphenicol). For example, M13-series vectors, pUC-series vectors, pBR322, pBluescript, pCR-Script, and such can be used. In addition to the above vectors, for example, pGEM-T, pDIRECT, and pT7 can also be used for the subcloning and excision of cDNAs. When an expression vector is expressed, for example, in *E. coli*, it should have the above characteristics in order to be amplified in *E. coli*. Additionally, when *E. coli* such as JM109, DH5α, HB101, or XL1-Blue are used as the host cell, the vector preferably has a promoter, for example, lacZ promoter (Ward et al. (1989) Nature 341:544-546; (1992) FASEB J. 6:2422-2427), araB promoter (Better et al. (1988) Science 240:1041-1043), or T7 promoter, that allows efficient expression of the desired gene in *E. coli*. Other examples of the vectors include pGEX-5X-1 (Pharmacia), "QIAexpress system" (QIAGEN), pEGFP, and pET (where BL21, a strain expressing T7 RNA polymerase, is preferably used as the host).

Furthermore, the vector may comprise a signal sequence for polypeptide secretion. When producing polypeptides into the periplasm of *E. coli*, the pelB signal sequence (Lei, S. P. et al. (1987) J. Bacteriol. 169:4379) may be used as a signal sequence for polypeptide secretion. For example, calcium chloride methods or electroporation methods may be used to introduce the vector into a host cell.

In addition to *E. coli*, expression vectors derived from mammals (e.g., pCDNA3 (Invitrogen), pEGF-BOS (Nucleic Acids Res. (1990) 18(17):5322), pEF, pCDM8), insect cells (e.g., "Bac-to-BAC baculovirus expression system" (GIBCO-BRL), pBacPAK8), plants (e.g., pMH1, pMH2), animal viruses (e.g., pHSV, pMV, pAdexLcw), retroviruses (e.g., pZIPneo), yeasts (e.g., "*Pichia* Expression Kit" (Invitrogen), pNV11, SP-Q01), and *Bacillus subtilis* (e.g., pPL608, pKTH50) may also be employed to express the mutant APCs of the present invention.

In order to express proteins in animal cells such as CHO, COS, and NIH3T3 cells, the vector preferably has a promoter necessary for expression in such cells, for example, an SV40 promoter (Mulligan et al. (1979) Nature 277:108), MMLV-LTR promoter, EF1α promoter (Mizushima et al. (1990) Nucleic Acids Res. 18:5322), CMV promoter, etc.). It is even more preferable that the vector also carries a marker gene for selecting transformants (for example, a drug-resistance gene selected by a drug such as neomycin and G418. Examples of vectors with such characteristics include pMAM, pDR2, PBK-RSV, pBK-CMV, pOPRSV, and pOP13, and such.

Examples of methods for expressing the mutant APCs of the present invention in animals include inserting a DNA of this invention into an appropriate vector, and introducing the vector into a living body by retrovirus methods, liposome methods, cationic liposome methods, adenovirus methods, and such. The vectors used in these methods include, but are not limited to, adenovirus vectors (e.g., pAdexlcw), retrovirus vectors (e.g., pZIPneo), and such. General gene manipulation techniques, such as inserting a DNA of the invention into a vector, can be performed by conventional methods (Molecular Cloning, 5.61-5.63). Administration to a living body may be performed by ex vivo or in vivo methods.

The present invention also provides cells transfected with the vectors of this invention. In a preferred embodiment of the present invention, the cells are those that artificially express the mutant APCs of this invention (for example, cells in which mutant APCs are artificially introduced and expressed). There are no particular limitations as to the kinds of cells into which the vectors of the present invention are introduced, and for example, *E. coli* and various animal cells may be used. In a preferred embodiment of the present invention, the cells are epithelial cells having the characteristic of piling up while maintaining cell-cell adhesion due to expression of the mutant APCs of this invention. The cells of the present invention are more preferably established cell lines that stably express the mutant APCs of this invention. Furthermore, the cells of the present invention are preferably cells derived from animals, and more preferably cells derived from *Xenopus laevis* (for example, A6 cells).

Cells that express the mutant APCs of this invention are considered to be similar to the actual cells that form polyps due to APC mutation. In Familial Adenomatous Polyposis (FAP) patients, normal cell-cell adhesion occurs at an early stage, and then benign polyps are formed, which are non-infiltrative and have yet to become malignant. Normally, several hundreds to several thousands of such polyps are formed, and if they are left alone and not excised, malignant cells develop from them due to mutations also in genes besides APC. At this point, canceration is considered to occur. Although cells expressing the mutant APCs of this invention represent a condition that mimics only APC mutations, these cells are useful as research materials for elucidating the causes of polyp formation or canceration.

Furthermore, the cells of the present invention are useful for screening compounds that inhibit piling up of cells. When the cells expressing the mutant APCs of this invention are *Xenopus laevis*-derived cells, the advantage is that the cells can be cultured at room temperature, in a carbon dioxide-free environment.

The cells of the present invention can be used as a production system to produce and express the mutant APCs of the present invention. The systems for producing mutant APCs include in vitro and in vivo systems. Production systems that use eukaryotic cells or prokaryotic cells are examples of in vitro production systems.

Eukaryotic host cells that can be used are, for example, animal cells, plant cells, and fungi cells. Mammalian cells, for example, CHO (J. Exp. Med. (1995) 108:945), COS, 3T3, myeloma, BHK (baby hamster kidney), HeLa, Vero, amphibian cells (e.g., *Xenopus* cells), or insect cells (e.g., Sf9, Sf21, Tn5) are known as animal cells. Among CHO cells, those defective in the DHFR gene, dhfr-CHO (Proc. Natl. Acad. Sci. USA (1980) 77:4216-4220), and CHO K-1 (Proc. Natl. Acad. Sci. USA (1968) 60:1275) are particularly preferable. Among animal cells, CHO cells are particularly preferable for large-scale expression. A vector can be introduced into a host cell by, for example, calcium phosphate methods, DEAE-dextran methods, methods using cationic liposome DOTAP (Boehringer-Mannheim), electroporation methods, and lipofection methods.

Useful prokaryotic cells comprise bacterial cells. As examples of bacterial cells, *E. coli* (for example, JM109, DH5α, HB101, and such), and also *Bacillus subtilis* are known.

These cells are transformed by a desired DNA, and the transformants are cultured in vitro to obtain a polypeptide. Transformants can be cultured using known methods. For example, the culture medium for animal cells may be a culture medium such as DMEM, MEM, RPMI1640, or IMDM, and may be used with or without serum supplements such as fetal calf serum (FCS).

Production systems using animal and plant hosts may be used as systems for producing polypeptides in vivo. For example, DNAs that encode the mutant APCs of the present invention can be introduced into those animal or plant hosts; the mutant APCs are produced in the body of the animal or plant and then recovered.

Animals to be used for the production system described above include mammals and insects. Mammals such as goats, pigs, sheep, mice, and cattle may be used (Vicki Glaser (1993) SPECTRUM Biotechnology Applications). Alternatively, the mammals may be transgenic animals.

For instance, DNAs that encode the mutant APCs of the present invention may be prepared as a fusion gene with a gene that encodes a polypeptide specifically produced in milk, such as the goat β casein gene. DNA fragments comprising the fusion gene are injected into goat embryos, which are then introduced back into female goats. The mutant APCs of this invention can be obtained from the milk produced by the transgenic goats (i.e., those born from the goats that received the modified embryos) or from their offspring. Appropriate hormones may be administered to increase the volume of milk containing the polypeptides produced by transgenic goats, (Ebert, K. M. et al., (1994) Bio/Technology 12:699-702).

Alternatively, insects such as silkworms may be used. Baculoviruses into which a DNA encoding the mutant APCs of this invention has been inserted, can be used to infect silkworms, and the mutant APCs can be recovered from body fluids (Susumu M. et al., (1985) Nature 315:592-594).

In addition, when using plants, tobacco, for example, can be used. When using tobacco, a DNA encoding a mutant APC of this invention may be inserted into a plant expression vector, such as pMON 530, which is then introduced into bacteria such as *Agrobacterium tumefaciens*. Then, the bacteria are used to infect tobacco such as *Nicotiana tabacum*, and the desired mutant APCs are recovered from the leaves (Julian K.-C. Ma et al., (1994) Eur. J. Immunol. 24:131-138).

The mutant APCs of the present invention, obtained as above, may be isolated from the inside or outside (the medium and such) of host cells, and purified as a substantially pure homogeneous polypeptide. Purification methods are not limited to any specific method. In fact, any standard method for isolating and purifying polypeptides may be used. For instance, column chromatography, filters, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify polypeptides.

Chromatographies such as affinity chromatography, ion-exchange chromatography, hydrophobic chromatography, gel filtration chromatography, reverse phase chromatography, and adsorption chromatography may be used (Strategies for Protein Purification and Characterization: A Laboratory Course Manual. Ed. Daniel R. Marshak et al., Cold Spring Harbor Laboratory Press (1996)). These chromatographies may be performed using liquid chromatographies such as HPLC and FPLC. The present invention provides highly purified mutant APCs purified by the above methods.

Generally, a widely-used assay for the Wnt signal transduction system involves the method of injecting a small amount of Wnt signal factor mRNA, antibody, and such into *Xenopus oocytes*, and examining the effects on development (Gloy, J., et al., Nat. Cell Biol. (2002) 4(5):351-357). This technique is also used for APC and for APC-binding proteins, such as β-catenin and axin, and phenomena such as formation of double-headed tadpoles and abnormal head-formation have lead to discussions on the function of APC and APC-binding proteins in the Wnt signal transduction system. Therefore, the purified mutant APCs of the present invention can also be used in this type of experiments.

Furthermore, this invention provides methods of screening for candidate compounds as agents that inhibit piling up of cells. The screening methods of this invention comprise the steps of: (a) contacting cells expressing a mutant APC of this invention with a test compound; (b) detecting piling up in these cells; and (c) selecting a compound that inhibits the piling up of cells.

The test compounds used in the screening methods of this invention are not particularly limited. Examples include libraries of synthetic low-molecular-weight compounds, purified proteins, gene library expression products, synthetic peptide libraries, cell extracts, and cell culture supernatants.

Usually, "contact" in step (a) mentioned above can be carried out by adding a test compound into a culture solution of cells expressing a mutant APC of this invention, but is not particularly limited to this method.

"Detecting piling up of cells" in step (b) mentioned above can be performed by those skilled in the art using the above-mentioned methods (for example, methods that use phase contrast microscopy and such).

In step (c) mentioned above, normally when the degree of piling up of cells is decreased compared to that when the test compound is not contacted with the cells, piling up of cells is considered to be inhibited.

Since piling up of cells is observed in many cancer cells, compounds that inhibit piling up of cells are expected to have antitumor activity. Therefore, compounds selected by the screening methods of this invention are expected to have antitumor activity. More specifically, agents that inhibit piling up of cells, which comprise these compounds as active ingredients, may become potential antitumor agents.

In conventional in vitro cell culture systems, "fibroblast" transformation assays with oncoproteins such as Ras and Src, are widely used. These assays are for observing, using a light microscope, the "focus" formation phenomenon that is caused by an increase of cells that do not adhere to anywhere since they continue to proliferate after the loss of anchorage dependence. In most cases when Ras, Src, or a number of oncogenes are expressed in epithelial cells, cell-cell adhesion and epithelial polarity are known to be lost, such that the cells take on a fibroblast or mesenchymal cell-like form. The cells of the present invention are cells that pile up while maintaining cell-cell adhesion, and thus differ from conventional cells. Therefore, the methods of this invention using these cells enable the screening of compounds that were difficult to obtain by conventional methods (for example, compounds that specifically inhibit the "piling up of epithelial cells").

Despite the fact that many cancers are derived from epithelial cells, the mainly used assay system that employed cultured cells were the "focus" formation assays, which use the above-mentioned fibroblasts. Development of assay systems that use epithelial cells may provide a more effective screening system against many kinds of cancer cells. The assay systems are also useful as materials for elucidating the mechanisms of how epithelial cells maintain monolayers.

The present invention comprises compounds obtained by the above-mentioned screening methods, and agents that inhibit piling up of cells or antitumor agents that contain these compounds as active ingredients.

The above-mentioned pharmaceutical agents of the present invention can be formulated by known pharmaceutical methods. For example, they can be formulated by appropriately combining with pharmaceutically acceptable carriers or vehicles, more specifically, sterilized water or physiological saline, vegetable oil, emulsifiers, suspending agents, surfactants, stabilizers, flavoring compounds, excipients, vehicles, preservatives, binding agents, and such, and by mixing at a unit dosage and form required by accepted pharmaceutical implementations.

Furthermore, the present invention relates to methods of screening for polynucleotides encoding mutant APCs, which can induce piling up of cells. The screening methods comprise the step of introducing a test polynucleotide into *Xenopus laevis*-derived cells to express mutant APC proteins, culturing these cells, detecting piling up of these cells, and selecting polynucleotides that cause the piling up of these cells.

In a preferred embodiment of the present invention, whether a polynucleotide encoding a subject's APC causes polyp development may be examined by using such a polynucleotide as a test sample. Usually, the test polynucleotide is inserted into an expression vector suitable for cellular expression, and then introduced into cells. Those skilled in the art can appropriately select an expression vector, and use standard genetic engineering techniques to construct an expression vector that carries this polynucleotide. This expression vector can be introduced into cells by known methods, such as the electroporation methods mentioned above, or lipofection methods.

An example of Xenopus laevis-derived cells used in the above-mentioned screening methods is A6 cells. Furthermore, piling up of cells can be detected by, for example, a method utilizing a phase contrast microscope. More specifically, a detailed observation of the cell morphology using the methods presented in the following Examples will enable detection of piling up of cells. In the present screening methods, a test polynucleotide is judged to code for a mutant APC that may induce piling up of cells, when piling up is observed in the cells expressed with the polynucleotide.

BRIEF DESCRIPTION OF THE DRAWINGS

FIG. 4 is a set of transmission electron microscope images showing piling up of cells expressing mutant APCs.

BEST MODE FOR CARRYING OUT THE INVENTION

The present invention will be explained in detail below with reference to Examples, but it is not to be construed as being limited thereto. The antibodies and cells used in Examples are as follows. Anti-Z0-1 monoclonal antibody (Clone: T8-754) and anti-DLG antibody (anti-PSD-95 Family, clone K28/86.2), were purchased from Sanko Junyaku and Upstate Biotechnology, respectively. TOTO-3 that selectively stains nucleic acids, and rhodamine-phalloidin that selectively stains actin filaments, were purchased from Molecular Probe. Nocodazole, a pharmaceutical agent that depolymerizes microtubules, was purchased from SIGMA. A6 cells (Xenopus laevis renal epithelial cell line) were grown in Leivobitz's L-15 medium containing 10% fetal calf serum (GIBCO BRL) at 23° C. in a carbon dioxide-free environment. The genes and cells of Xenopus laevis were chosen because of the reason described in Example 2.

Example 1

Figure 1:
FIG. 1 shows a block diagram of Xenopus laevis APC protein domains, and a schematic diagram of the GFP-fused full-length and mutant APCs used in the present invention.

Construction of Autofluorescent Protein GFP (Green Fluorescent Protein)-Fused APCs In order to elucidate APC function in detail, a routine procedure was used to prepare expression vectors in which cDNAs carrying different APC sites were fused with the cDNA of an auto fluorescent protein, GFP (green fluorescent protein) (FIG. 1).

The Xenopus laevis APC gene sequence is known and is described in GenBank (U64442). The individual expression vectors were produced by the following procedure.

(a) GFP-fAPC: a vector for expressing GFP-fused full-length APC. Expression vectors, pGFP-C(NheI)/APC(1-8490) and pQBI25/APC(1-8487), which carry full-length APCs have already been reported in the present inventors' publications. In order to construct a GFP-fAPC expression vector, first, a cDNA containing the 3' region of APC, which had been excised from pGFP-C(NheI)/APC(1-8490) using XbaI, was inserted into the XbaI site of pEGFP-C1 (Clontech). Then, to the SacII-BamHI site of this vector, cDNA excised from pQBI25/APC(1-8487) using SacII and BamHI was inserted. Finally, cDNA excised from pGFP-C(NheI)/APC(1-8490) using BamHI and NotI was inserted into the BamHI-NotI site of this vector. A vector containing a full-length APC (APC/PEGFP-C1) was thus constructed.

(b) GFP-APC(ΔTSV): a vector expressing TSV-deleted APC. TSV is three amino acids at the APC C-terminus. A gene encoding amino acids 2089-2826 of APC was produced by PCR using pGFP-C(NheI)/APC(1-8490) as the template and the following primers:

```
                                         (SEQ ID NO: 2)
CGACGCGTAATGCATTTTCTCCAGACTCTG,
and (SEQ ID NO: 3)
GGAATTCGGATCCTCACACCAGATAAGAACCAGAGTGCC.
```

This PCR product was cleaved with SpeI and EcoRI, and then inserted into the NheI-EcoRI site of pGFP-C(NheI) vector (APC(6475-8478)/pGFP-C(NheI)). This vector was cleaved with PvuI and NotI, and the obtained fragment was inserted into APC/pEGFP-C1 cleaved with the same enzymes.

(c) ΔcAPC-GFP: the expression vector for this protein has already been reported in the inventors' publications.

(d) nAPC-GFP: a vector expressing only the N-terminal region of APC (comprising the heptad domain and armadillo domain). A gene encoding 859 amino acids of the APC N-terminus was produced by PCR using pGFP-C(NheI)/APC(1-8490) as the template, and the following primers:

```
CGACGCGTATGGCTGCTGCTTCGTATGATCAGT,   (SEQ ID NO: 4)
and

CGACGCGTACCTGCTGTTCTTTCCCTGTC.       (SEQ ID NO: 5)
```

This PCR product was cleaved with MluI, and inserted into the MluI site of pGFP(MluI) vector (reported by the inventors).

(e) n2APC-GFP: a vector expressing only the coiled-coil heptad domain of the APC N-terminal region. A gene that encodes 284 amino acids of the APC N-terminus was produced by PCR using pGFP-C(NheI)/APC(1-8490) as the template, and the following primers:

```
5' CTAGCTAGCATGGCTGCTGCTTCGTATG 3',    (SEQ ID NO: 6)
and

3' CCTGTCCCAAGTAGGTCACGATCGATC 5'.     (SEQ ID NO: 7)
```

This PCR product was cleaved with NheI, and inserted into the NheI site of pQBI25 vector.

(f) MAPC-GFP: a vector expressing only the central region of APC. First, a gene encoding APC amino acids 860-1120 was produced by PCR using the following primers:

```
    CTAGCTAGCCTCGGCAACTACCATTCG,       (SEQ ID NO: 8)
    and

ATTAGAGCTCACTCTAGAC.               (SEQ ID NO: 9)
```

This PCR product was cleaved with NheI and XbaI, and then inserted into the NheI site of pQBI25 vector. Subsequently, this vector was cleaved with EcoRI, and inserted with a fragment containing the central region of APC, which was cutout from ΔcAPD-GFP with EcoRI. Finally, this vector was cleaved with HindIII and ApaI, and inserted with a fragment cut out from ΔcAPC-GFP using HindIII and ApaI.

(g) GFP-cAPC: a vector expressing only the C-terminal region of APC. The expression vector of this protein has already been reported in the inventors' publication (Mimori-Kiyosue et al., J. Cell Biol., 148(3):505-18, 2000).

Example 2

Transfer of cDNAs into A6 Cells and Screening

The inventors established cell lines with stable expression by introducing the vectors obtained in Example 1 into A6 cells.

APC expression is extremely difficult in many mammalian culture cell lines. Although cells that conditionally express full-length APCs have been reported to date (Mori, P. J. et al., Proc. Natl. Acad. Sci. USA 93 (15): 7950-4, 1996), there are no reports on the establishment of cell lines that stably express foreign full-length and truncated APCs. Therefore, whether A6 cells are appropriate for expressing APC was examined.

First, a preliminary experiment was performed, in which A6 cells were expressed with GFP-tag only using a pQBI25 vector (QBIOgene) and Effectene transfection reagent (Qiagen). GFP expression was confirmed by observation of a fluorescence-staining image under a fluorescence microscope. Cells expressing a distinct fluorescence signal other than that of GFP were not found in the investigation. Cells were cultured starting at 48-72 hours after pQBI25 vector transfection in the presence of 0.6-0.8 mg/mL of G418 sulfate (Calbiochem), and resistant clones were selected. This confirmed that A6 cells readily form colonies of resistant clones. Furthermore, the expression vectors of Example 1 were introduced, and proliferation of cells emitting GFP fluorescence was confirmed. These experiments were performed at the standard culturing conditions for A6 cells: room temperature and a carbon dioxide-free environment. These results confirmed that this cell line is appropriate for visual screening of proteins that are expressed from GFP-fused APCs.

Each of the cDNAs presented in Example 1 was introduced into cells under conditions similar to those described above, and screening was performed by detecting GFP fluorescence under a fluorescence microscope. Cell lines showing stable expression of each construct were established. After establishing stably expressing cell lines, the status of mutant APC expression could be monitored easily by GFP fluorescence without further manipulating the cells, and cellular localization of mutant APC in viable cells could be detected.

Example 3

Figure 2:
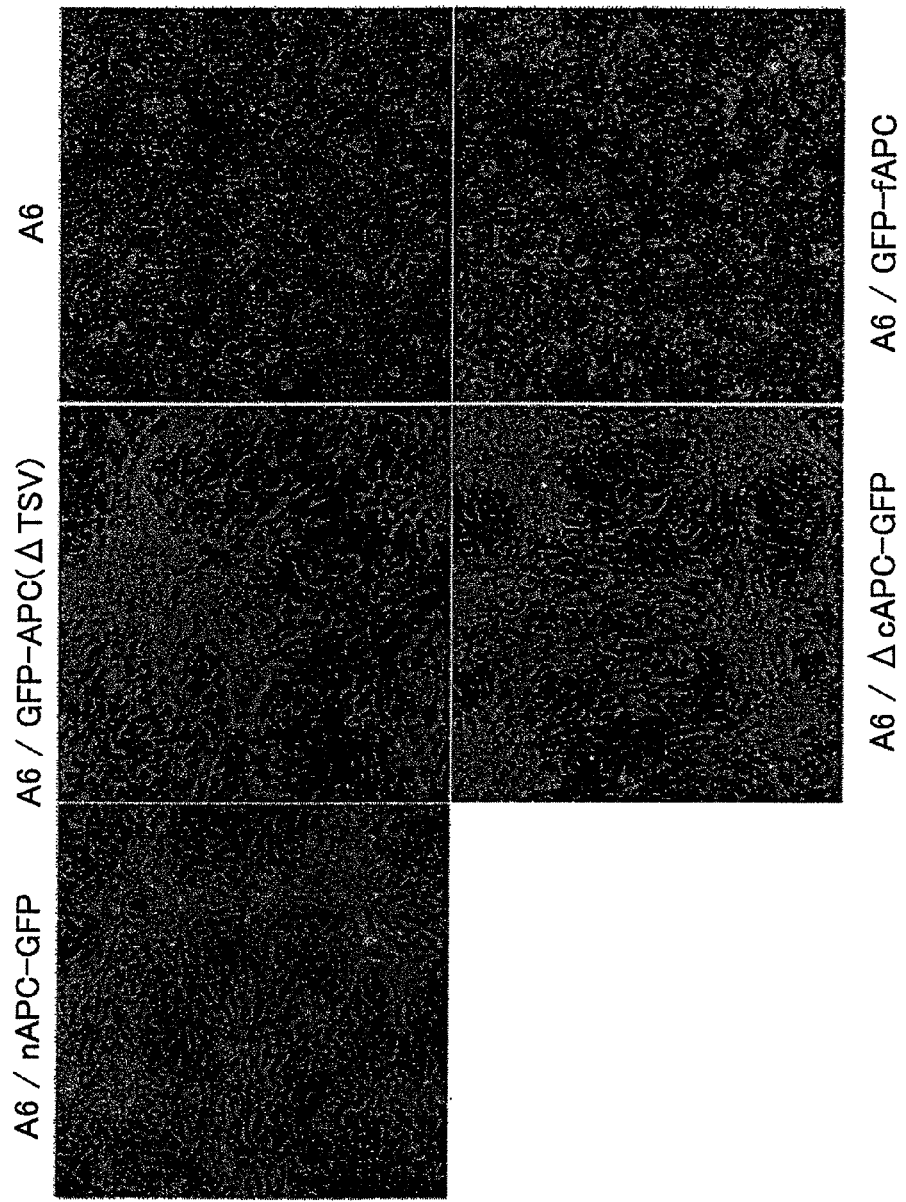
FIG. 2 shows a set of phase-contrast images of parental A6 cells, and A6 cell lines stably expressing GFP-fAPC, GFP-APC(ΔTSV), ΔcAPC-GFP, and nAPC-GFP.

Morphological Observation of Cells Expressing GFP-Fused Full-Length and Truncated APCs by Phase Contrast Microscopy The morphology of cells expressing GFP-fused full-length and truncated APCs obtained in Example 2 was observed by phase contrast microscopy, and compared to that of the parental A6 cells. Cells were widely spread on a dish at 100% confluency, and cultured for five days or more with a medium exchange every day, until the cells became dense and polarized to an epithelial structure. Parental A6 cells and GFP-fAPC-expressing cells formed a flat monolayer structure having the morphology of an epithelium. However, in GFP-APC (ΔTSV), ΔcAPC-GFP, or nAPC-GFP-expressing cells, bulging regions instead of a flat layer are formed at a certain frequency (FIG. 2). Similar bulging regions were also observed in n2APC-GFP-expressing cells. However, bulging regions were not observed in all of the strains, and were restricted to the cells where the existing GFP fluorescence intensity was high, or more specifically, to cells with high n2APC-GFP expression levels. In order for the cells to form bulges by n2APC-GFP, the expression level had to be approximately ten times of that of GFP-APC(ΔTSV), ΔcAPC-GFP, or nAPC-GFP, as measured by their cellular fluorescence intensities.

Example 4

Figure 3:
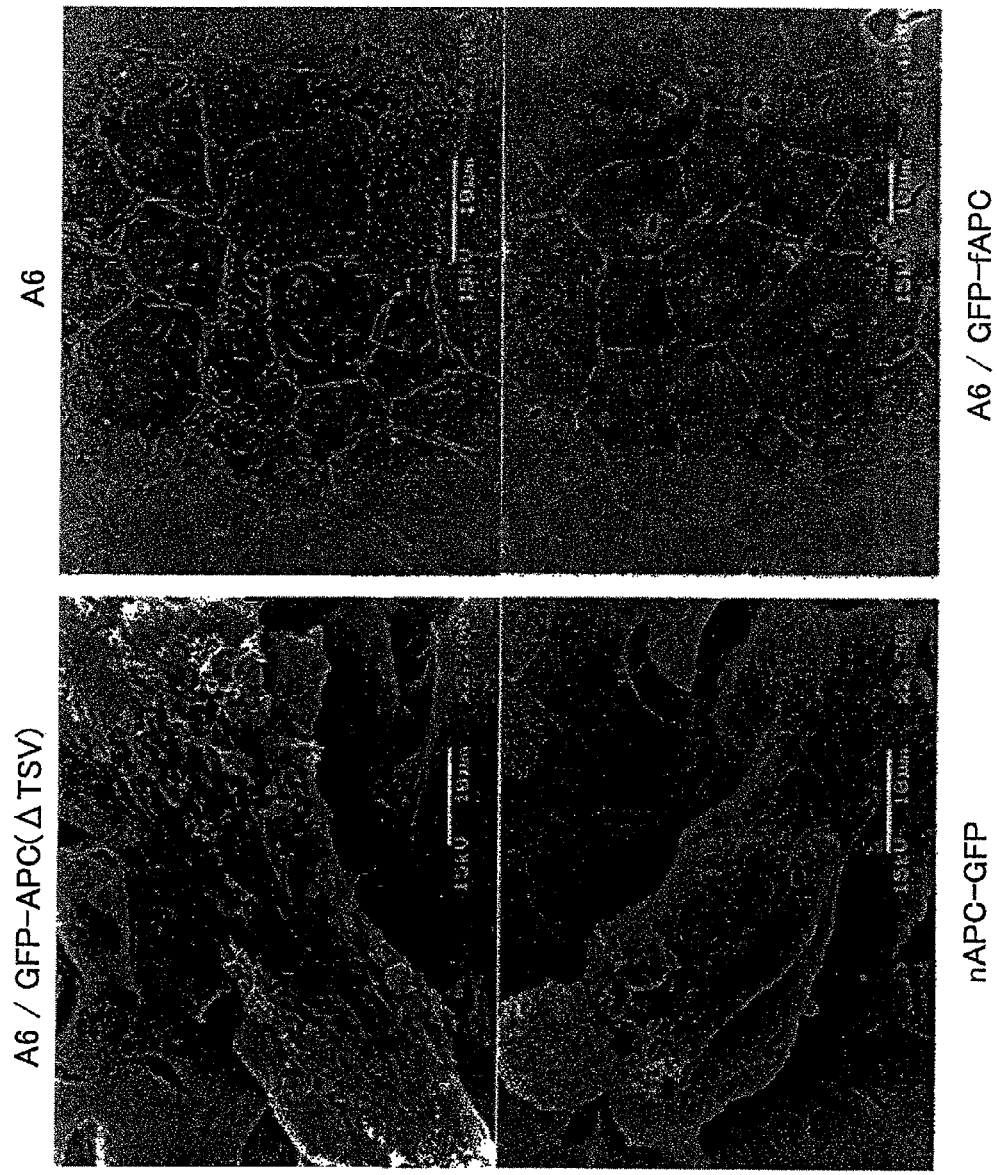
FIG. 3 is a set of scanning electron microscope images showing piling up of cells expressing mutant APCs.

Electron Microscopic Observation of GFP-Fused Full-Length APC- and Truncated APC-Expressing Cells Electron microscopic observation was carried out for a detailed examination of the morphology of GFP-fused full-length and truncated APC-expressing cells obtained in Example 2 (FIG. 3). Each of the cells was fixated in a 1% glutaraldehyde aqueous solution, prepared using a phosphate buffer. Sample preparation was carried out by routine procedures, and the cell surface structure was examined by scanning electron microscopy. In parental A6 cells and GFP-fAPC-expressing cells, the apical membrane of closely packed cells extended as a flat surface, and only protrusions of the microvillar and primary ciliary structures on the apical membrane were observed. In contrast, in GFP-APC(ΔTSV), ΔcAPC-GFP, and nAPC-GFP-expressing cells, several to several tens of cells formed protrusions, and regions that do not form flat cellular monolayers appeared.

Next, ultrathin sections of cells fixated in 1% glutaraldehyde aqueous solution were prepared by routine procedures, and longitudinal sections of the cells were observed by transmission electron microscopy (FIG. 4). Parental A6 cells formed a monolayer with a certain degree of intercellular space, whereas GFP-APC(ΔTSV), ΔcAPC-GFP, and nAPC-GFP-expressing cells had increased intercellular space and cell-substrate space, and clearly showed piling up of cells. Regardless of this, a typical intercellular adhesive structure was confirmed to be maintained. That is to say, despite the fact that tight junctions and adherens junctions, which are intercellular adhesive structures characteristic of the apical region of a cell, were observed in mutant APC-expressing cells according to electron microscope images, underneath these junctions, intercellular space and cell-substrate space were significant. On the contrary, in GFP-fAPC-expressing cells, absolutely no cell-cell and cell-substrate space were observed, and the cells formed parallel rows with the monolayer. These results showed that although APC has a function of strengthening cell-cell adhesion, mutant APCs do not have this function, and that both cell-cell and cell-matrix adhesions are weakened, probably by a dominant negative effect.

More specifically, whereas full-length APC has a function of strengthening cell-cell and cell-matrix adhesions, this function is lost in mutant APCs without the C-terminus; cells are detached from the matrix due to dominant negative effects and then become piled up.

Although the reason why n2APC-GFP requires a high expression level for cells to pile up (has low cell piling up activity) is still unknown, the following two possibilities were considered. 1) APC is reported to form a homodimer with its coiled-coil region at N-terminus (Joslyn, G., et. al., Proc. Natl. Acad. Sci. USA. 1993; 90(23):11109-13). However, stable complex formation within cells seems to require also the armadillo repeat region since n2PAC-GFP can hardly co-localize with endogenous full-length APC while nAPC-GFP strongly co-localizes with APC. Accordingly, mutants that can form a stable complex with endogenous APC are more likely to exhibit dominant negative effects. 2) Asef, a regulatory factor of the actin skeleton, is reported to bind to the armadillo repeat region to enhance cell motility (Kawasaki, Y., et al., Science (2000) 289(5482), 1194-1197), therefore, cellular adhesion and morphology might have altered due to the synergistic effects of a dominant negative effect and enhanced cell motility by Asef.

Example 5

Figure 5:
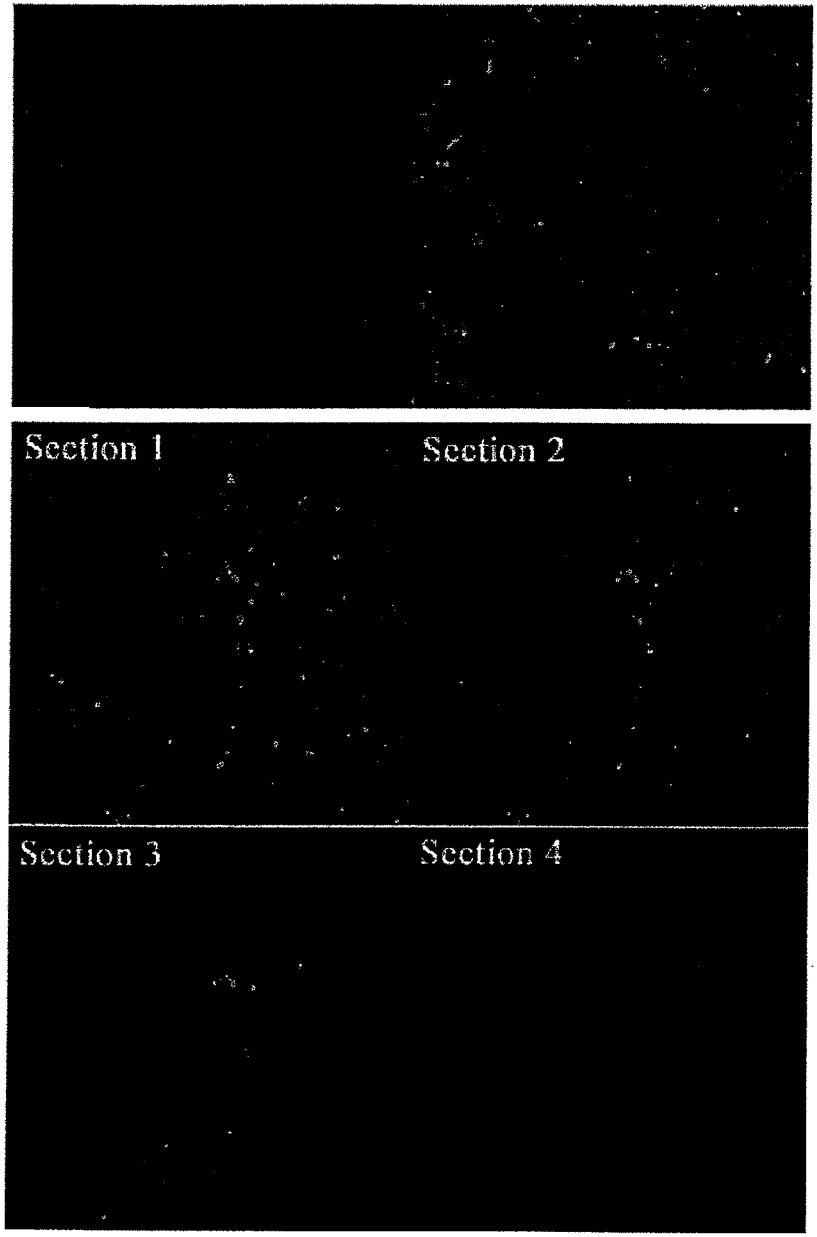
FIG. 5 demonstrates that even after piling up of cells expressing mutant APCs, cells form an intercellular adhesive structure. TJ protein Z0-1 was stained with anti-Z0-1 antibody.

Fluorescence Microscopic Observation of GFP-Fused Full-Length APC- and Truncated APC-Expressing Cells The intercellular adhesive structures of GFP-fused full-length APC- and truncated APC-expressing cells obtained in Example 2 were immunostained using anti-Z0-1 antibody, observed by fluorescence confocal microscopy, and compared with that of the parental A6 cells (FIG. 5). Z0-1 is a component of tight junction (TJ), which is one of the intercellular adhesive units in the epithelial or endothelial cell layer. At the apical plasma membrane of cells that have normal epithelial polarity, Z0-1 is distributed in the continuous border surrounding the cell. In A6 cells and GFP-fAPC-expressing cells, Z0-1 was observed to be continuously present along the cellular border, and the cells were observed to have a normal epithelial morphology. In GFP-APC (ΔTSV), ΔcAPC-GFP, and nAPC-GFP-expressing cells, normal staining of Z0-1 was observed in regions where cells are not piled up, and even in the piled up regions, continuous strands of Z0-1 were observed. This result showed that the cells expressing GFP-APC(ΔTSV), ΔcAPC-GFP, and nAPC-GFP undergo piling-up while maintaining the intercellular adhesions (TJ, AJ).

These findings showed that mutant APCs affect cellular morphology, and inhibit the monolayering of normal epithelial cells. Since piled up cells maintain intercellular adhesions (TJ, AJ), which resembles the polyp formation phenomenon in model mice, these cells can be used as a model system.

Example 6

Cellular Localization of Full-Length APC and Mutant APCs

GFP-fAPC was localized in the basolateral membrane and junction regions of A6 cells, which have taken on the morphology of polarized epithelial cells. The present inventors have reported in literature that a similar construct, fAPC-mGFP (a publicly disclosed full-length APC construct where GFP is inserted inside of the APC), is localized in the basolateral membrane of A6 cells (Mimori-Kiyosue, Y. and Tsukita, S., J. Cell Biol., 154(6):1105-1109, 2001). However, localization of GFP-APC(ΔTSV), ΔcAPC-GFP, mAPC-GFP, nAPC-GFP, and n2APC-GFP in the basolateral membrane was markedly inhibited. Therefore, APC is considered to be localized in the basolateral membrane and junction regions due to TSV, its C-terminal PDZ binding motif. Since DLG, one of the PDZ proteins localized in the basolateral membrane and junction regions, is reported to bind to the APC C-terminus (Matsumine, A., et al., Science. 1996; 272 (5264): 1020-3), APC localization in the basolateral membrane and junction regions is considered to be dependent on PDZ-proteins such as DLG.

In A6 cells that have become polarized and formed cell-cell adhesions, nAPC-GFP was found to be localized in the junction regions. However, this localization was different from that of full-length APC, which can localize not only to the junction regions but also to the basolateral membrane. Therefore, nAPC-GFP is considered to maintain only the binding with some of the APC binding proteins: junction-localized proteins.

Figure 6:
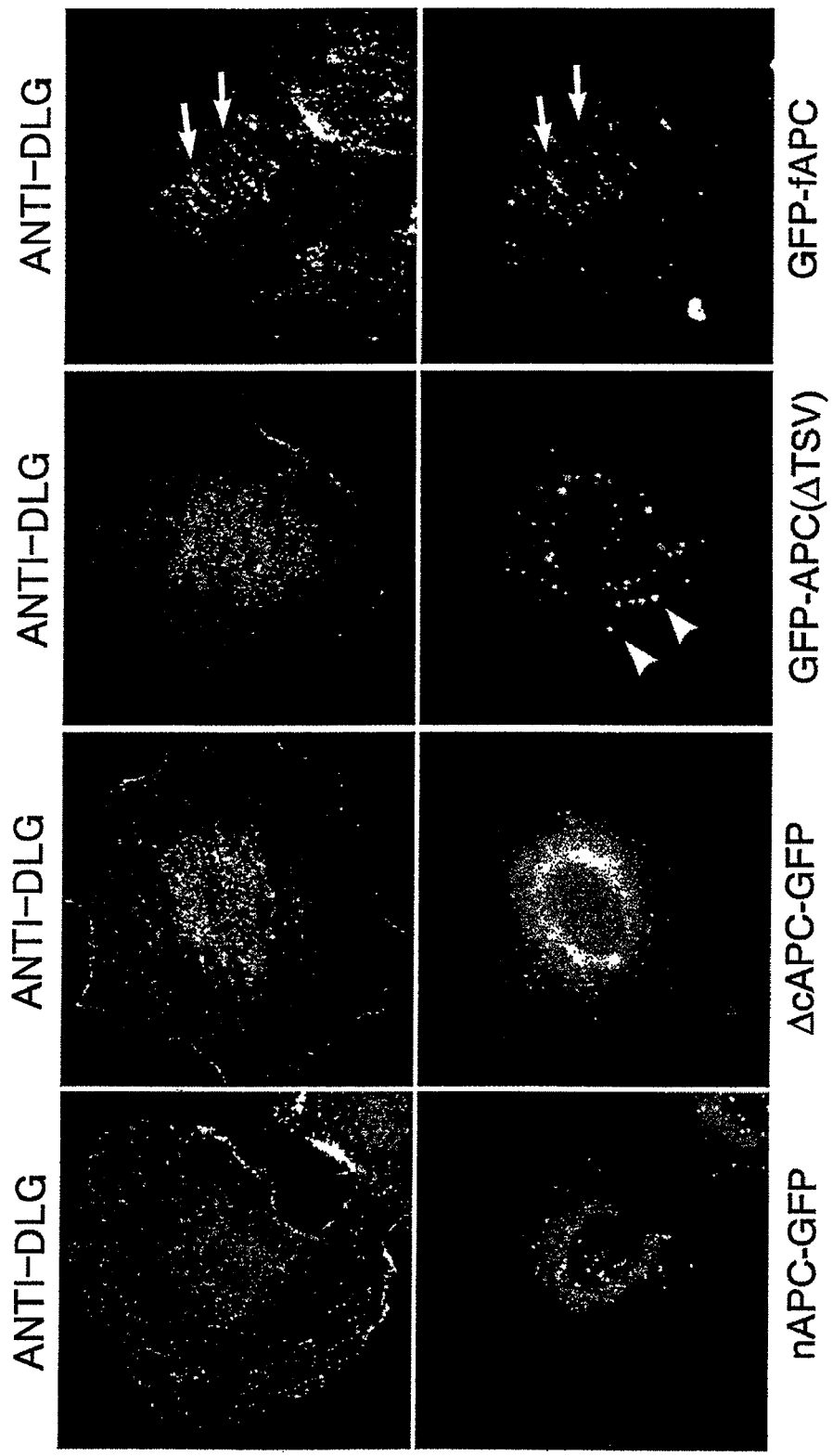
FIG. 6 is a set of fluorescence microscope images showing localization of GFP-fAPC, GFP-APC(ΔTSV), ΔcAPC-GFP, and nAPC-GFP, together with DLG localization, in the absence of microtubules in non-polarized A6 cells. GFP-fAPC co-localizes with DLG in a striated manner (arrows), while GFP-APC(ΔTSV) is dispersed in the cytoplasm (arrow heads) and does not co-localize with DLG.

Furthermore, when microtubules were completely depolymerized by adding a microtubule-depolymerizing agent (nocodazole) under conditions in which cell density is low and cell-cell adhesion is not seen, GFP-fAPC that was localized on the microtubules moved to the basal side of the cell membrane, distributed in a striated pattern, and co-localized with DLG (FIG. 6). However, GFP-APC(ΔTSV), ΔcAPC-GFP, mAPC-GFP, nAPC-GFP, and n2APC-GFP were dispersed in the cytoplasm; DLG co-localization and the formation of a striated pattern as in GFP-fAPC was not observed. These results showed that APC binding to the basal side of the cell membrane requires the binding of PDZ proteins, such as DLG, in a manner that depends on TSV, a PDZ binding motif at the C-terminus of APC.

Example 7

Cell Spreading Activity Analysis of Full-Length APC and Mutant APCs

Figure 7:
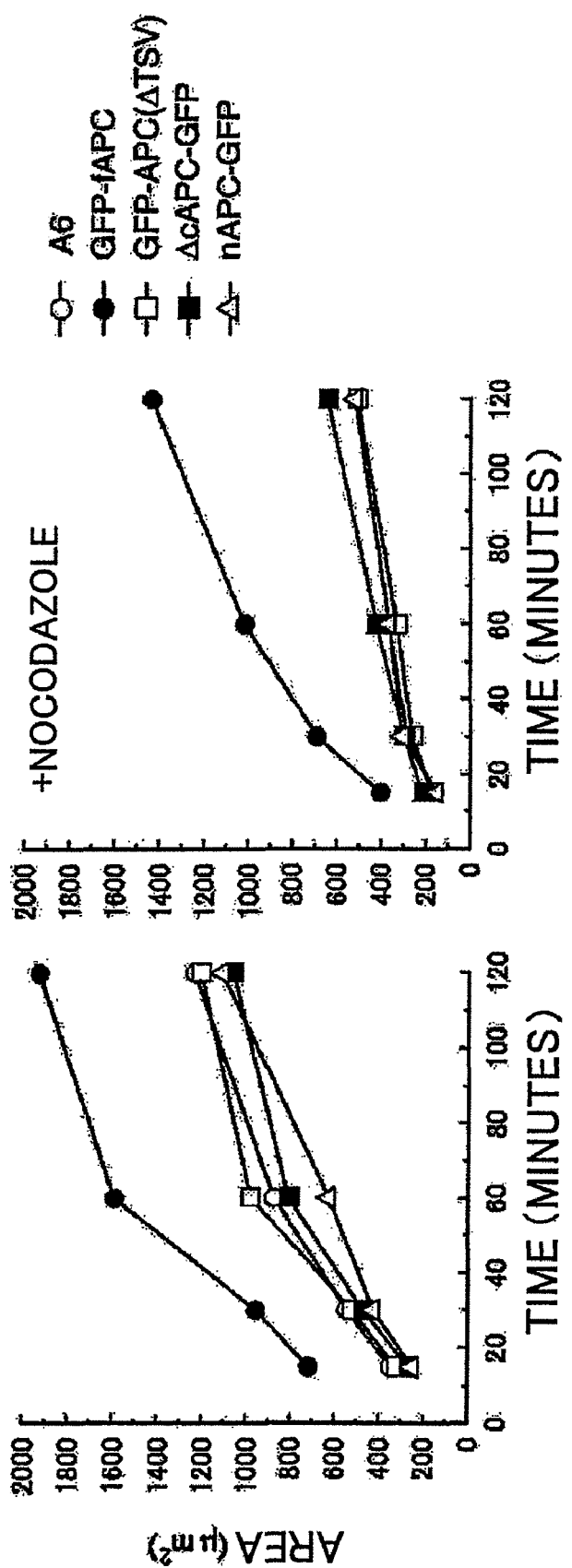
FIG. 7 is an area plot of cells at a given period of time after parental A6 cells and cells expressing GFP-fAPC, GFP-APC(ΔTSV), ΔcAPC-GFP, and nAPC-GFP are plated. Assays were performed in the absence of nocodazole, as shown on the left; and under conditions in which the microtubules were depolymerized in the presence of nocodazole, as shown on the right.

Next, cell spreading assays were performed to examine the effects of full-length APC and mutant APCs on cell motility. Each of the cell lines was treated with trypsin, collected from dish, and plated onto cover glasses. The cover glasses were taken out for fixation 15, 30, 60, and 120 minutes later, and actin was stained with rhodamine-phalloidin to visualize cell shape. Each sample was photographed under a fluorescence microscope, area of the region of cells stained with rhodamine-phalloidin was measured, and the average area for each cell was determined and plotted (FIG. 7). As a result, cell spreading was significantly enhanced only in cells expressing fAPC-GFP. Next, to examine whether cell spreading activity is due to the stabilization of microtubules, a similar assay was performed under conditions in which the microtubules were depolymerized by nocodazole addition. As expected, significantly enhanced cell spreading was only observed in GFP-fAPC-expressing cells. These results showed that in addition to stabilizing microtubules, APC has cell spreading activity, and that the PDZ-binding function at the C-terminus is important for this activity. As indicated by the APC localization shown in Example 6, since APC localizes to the basolateral membrane by binding to PDZ proteins such as DLG via its C-terminal PDZ-binding motif, localization to the cell membrane via PDZ proteins is considered necessary for normal APC function. Mutant APCs do not have the function of binding to cell membrane and cannot express normal functions. Moreover, they are considered to exhibit dominant negative effects.

These results suggest that APC localizes to the cell membrane by binding to PDZ proteins through its C-terminus, and contributes to the regulation of cell motility and maintenance of cell morphology.

INDUSTRIAL APPLICABILITY

The present invention provides mutant APC proteins which can induce piling up of cells. Cells expressing these proteins are useful for screening compounds that inhibit piling up of cells. Furthermore, the present inventors elucidated, for the first time, that cells expressing mutant APCs maintain the intercellular adhesive structure, and yet exhibit piling up of cells. Elucidation of the mechanisms of polyp formation and malignant formation from these findings is very much expected.

What is claimed is:

1. An isolated polynucleotide that encodes a mutant adenomatous polyposis coli (APC) protein which induces piling up of cells, wherein the APC protein consists of:
   (i) a sequence having 95% identity or higher to amino acids 1-2826 of SEQ ID NO:1; or
   (ii) a sequence having 95% identity to amino acids 1-2158 of SEQ ID NO:1.

2. A vector that comprises the polynucleotide of claim 1.

3. An isolated cell that comprises an artificially expressed mutant APC protein encoded by the polynucleotide of claim 1.

4. The cell of claim 3, which is a mammalian cell.

5. The cell of claim 3, which is a *Xenopus laevis* cell.

6. The cell of claim 3, which is an established cell line.

7. The polynucleotide of claim 1, wherein the mutant APC protein consists of amino acids 1-2826 of SEQ ID NO:1 or amino acids 1-2158 of SEQ ID NO:1.

8. The polynucleotide of claim 1 or 7, wherein the mutant APC protein is a *Xenopus laevis* protein.

\* \* \* \* \*

SEQUENCE LISTING

```
<160> NUMBER OF SEQ ID NOS: 9

<210> SEQ ID NO 1
<211> LENGTH: 2829
<212> TYPE: PRT
<213> ORGANISM: Xenopus laevis

<400> SEQUENCE: 1

Met Ala Ala Ala Ser Tyr Asp Gln Leu Val Lys Gln Val Glu Ala Leu
 1               5                  10                  15

Thr Met Glu Asn Thr Asn Leu Arg Gln Glu Leu Glu Asp Asn Ser Asn
             20                  25                  30

His Leu Thr Lys Leu Glu Thr Glu Ala Thr Asn Met Lys Glu Val Leu
         35                  40                  45

Lys Gln Leu Gln Gly Ser Ile Glu Asp Glu Ala Met Ala Ser Ser Gly
     50                  55                  60

Pro Ile Asp Leu Leu Glu Arg Phe Lys Asp Leu Asn Leu Asp Ser Ser
 65                  70                  75                  80

Asn Ile Pro Ala Gly Lys Ala Arg Pro Lys Met Ser Met Arg Ser Tyr
                 85                  90                  95

Gly Ser Arg Glu Gly Ser Leu Ser Gly His Ser Gly Glu Cys Ser Pro
            100                 105                 110

Val Pro Val Gly Ser Phe Gln Arg Arg Gly Leu Leu Asn Gly Ser Arg
        115                 120                 125

Glu Ser Ala Gly Tyr Met Glu Glu Leu Glu Lys Glu Arg Leu Leu Leu
    130                 135                 140

Ile Ala Glu His Glu Lys Glu Glu Lys Glu Lys Arg Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Met Gln Thr Asp Met Thr Arg Arg Gln Leu Glu Tyr Glu
            180                 185                 190

Ala Arg Gln Ile Arg Ala Ala Met Glu Glu Gln Leu Gly Thr Cys Gln
        195                 200                 205

Asp Met Glu Lys Arg Val Gln Thr Arg Val Gly Lys Ile His Gln Ile
    210                 215                 220

Glu Glu Glu Ile Leu Arg Ile Arg Gln Leu Leu Gln Ser Gln Val Ala
225                 230                 235                 240

Glu Ala Ala Glu Arg Thr Pro Gln Ser Lys His Asp Ala Gly Ser Arg
                245                 250                 255
```

-continued

```
Asp Ala Glu Lys Leu Pro Asp Gly Gln Gly Thr Ser Glu Ile Thr Ala
            260                 265                 270

Ser Gly Asn Val Gly Ser Gly Gln Gly Ser Ser Ser Arg Ala Asp His
        275                 280                 285

Asp Thr Thr Ser Val Met Ser Ser Asn Ser Thr Tyr Ser Val Pro Arg
    290                 295                 300

Arg Leu Thr Ser His Leu Gly Thr Lys Val Glu Met Val Tyr Ser Leu
305                 310                 315                 320

Leu Ser Met Leu Gly Thr His Asp Lys Asp Met Ser Arg Thr Leu
            325                 330                 335

Leu Ala Met Ser Ser Gln Asp Ser Cys Ile Ala Met Arg Gln Ser
            340                 345                 350

Gly Cys Leu Pro Leu Leu Ile Gln Leu Leu His Gly Asn Asp Lys Asp
            355                 360                 365

Ser Val Leu Leu Gly Asn Ser Arg Gly Ser Lys Glu Ala Arg Ala Ser
        370                 375                 380

Gly Ser Ala Ala Leu Asp Asn Ile Ile His Ser Gln Pro Asp Asp Lys
385                 390                 395                 400

Arg Gly Arg Arg Glu Ile Arg Val Leu His Leu Leu Glu Gln Ile Arg
                405                 410                 415

Ala Tyr Cys Glu Thr Cys Trp Glu Trp Gln Glu Ala His Glu Gln Gly
            420                 425                 430

Met Asp Gln Asp Lys Asn Pro Met Pro Ala Pro Val Asp His Gln Ile
            435                 440                 445

Cys Pro Ala Val Cys Val Leu Met Lys Leu Ser Phe Asp Glu Glu His
            450                 455                 460

Arg His Ala Met Asn Glu Leu Gly Gly Leu Gln Ala Ile Ala Glu Leu
465                 470                 475                 480

Leu Gln Val Asp Cys Glu Met Tyr Gly Leu Ile Asn Asp His Tyr Ser
                485                 490                 495

Val Thr Leu Arg Arg Tyr Ala Gly Met Ala Leu Thr Asn Leu Thr Phe
            500                 505                 510

Gly Asp Val Ala Asn Lys Ala Thr Leu Cys Ser Met Lys Ser Cys Met
            515                 520                 525

Arg Ala Leu Val Ala Gln Leu Lys Ser Glu Ser Glu Asp Leu Gln Gln
            530                 535                 540

Val Ile Ala Ser Val Leu Arg Asn Leu Ser Trp Arg Ala Asp Val Asn
545                 550                 555                 560

Ser Lys Lys Thr Leu Arg Glu Val Gly Ser Val Lys Ala Leu Met Glu
                565                 570                 575

Cys Ala Leu Asp Val Lys Lys Glu Ser Thr Leu Lys Ser Val Leu Ser
            580                 585                 590

Ala Leu Trp Asn Leu Ser Ala His Cys Thr Glu Asn Lys Ala Asp Ile
            595                 600                 605

Cys Ser Val Asp Gly Ala Leu Ala Phe Leu Val Ser Thr Leu Thr Tyr
            610                 615                 620

Arg Ser Gln Thr Asn Thr Leu Ala Ile Ile Glu Ser Gly Gly Gly Ile
625                 630                 635                 640

Leu Arg Asn Val Ser Ser Leu Ile Ala Thr Asn Glu Asp His Arg Gln
                645                 650                 655

Ile Leu Arg Glu Asn Asn Cys Leu Gln Thr Leu Leu Gln His Leu Lys
            660                 665                 670

Ser His Ser Leu Thr Ile Val Ser Asn Ala Cys Gly Thr Leu Trp Asn
```

```
                    675                 680                 685
Leu Ser Ala Arg Asn Ala Lys Asp Gln Glu Gly Leu Trp Asp Met Gly
            690                 695                 700
Ala Val Ser Met Leu Lys Asn Leu Ile His Ser Lys His Lys Met Ile
705                 710                 715                 720
Ala Met Gly Ser Ala Ala Leu Arg Asn Leu Met Ala Asn Arg Pro
                725                 730                 735
Ala Lys Tyr Lys Asp Ala Asn Ile Met Ser Pro Gly Ser Val Pro
            740                 745                 750
Ser Leu His Val Arg Lys Gln Lys Ala Leu Glu Ala Glu Leu Asp Ala
            755                 760                 765
Gln His Leu Ser Glu Thr Phe Asp Asn Ile Asp Asn Leu Ser Pro Lys
    770                 775                 780
Thr Thr His Arg Asn Lys Gln Arg His Lys Gln Asn Leu Cys Ser Glu
785                 790                 795                 800
Tyr Ala Leu Asp Ser Ser Arg His Asp Asp Ser Ile Cys Arg Ser Asp
                805                 810                 815
Asn Phe Ser Ile Gly Asn Leu Thr Val Leu Ser Pro Tyr Ile Asn Thr
            820                 825                 830
Thr Val Leu Pro Gly Ser Ser Ser Pro Arg Pro Thr Met Asp Gly Ser
    835                 840                 845
Arg Pro Glu Lys Asp Arg Glu Arg Thr Ala Gly Leu Gly Asn Tyr His
850                 855                 860
Ser Thr Thr Glu Ser Ser Gly Asn Ser Ser Lys Arg Ile Gly Ile Gln
865                 870                 875                 880
Leu Ser Thr Thr Ala Gln Ile Ser Lys Val Met Asp Glu Val Ser Asn
                885                 890                 895
Ile His Leu Val Gln Glu Asn Arg Ser Ser Gly Ser Ala Ser Glu Met
            900                 905                 910
His Cys Met Ser Asp Glu Arg Asn Ser Gln Arg Lys Pro Ser Ser Asn
            915                 920                 925
His Pro Gln Ser Asn Pro Phe Thr Phe Thr Lys Ala Glu Ser Ser Thr
    930                 935                 940
Arg Gly Cys Pro Val Ala Phe Met Lys Met Glu Tyr Lys Met Ala Ser
945                 950                 955                 960
Asn Asp Ser Leu Asn Ser Val Ser Ser Thr Glu Gly Tyr Gly Lys Arg
                965                 970                 975
Gly Gln Val Lys Pro Ser Val Glu Ser Tyr Ser Glu Asp Glu Ser
            980                 985                 990
Lys Phe Phe Ser Tyr Gly Gln Tyr Pro Ala Gly Leu Ala His Lys Ile
    995                 1000                1005
Gln Ser Ala Asn His Met Asp Asp Asn Asp Thr Glu Leu Asp Thr Pro
    1010                1015                1020
Ile Asn Tyr Ser Leu Lys Tyr Ser Asp Glu Leu Asn Ser Gly Arg
1025                1030                1035                1040
Gln Ser Pro Thr Gln Asn Glu Arg Trp Ser Arg Pro Lys His Ile Ile
                1045                1050                1055
Asp Ser Glu Met Lys Gln Ser Glu Gln Arg Gln Pro Arg Thr Thr Lys
            1060                1065                1070
Thr Thr Tyr Ser Ser Tyr Thr Glu Asn Lys Glu Glu Lys His Lys Lys
            1075                1080                1085
Phe Pro Pro His Phe Asn Gln Ser Glu Asn Val Pro Ala Tyr Thr Arg
    1090                1095                1100
```

-continued

```
Ser Arg Gly Ala Asn Asn Gln Val Asp Gln Ser Arg Val Ser Ser Asn
1105                1110                1115                1120

Leu Ser Asn Asn Ser Lys Ala Ser Lys Pro His Cys Gln Val Asp Asp
            1125                1130                1135

Tyr Asp Asp Asp Lys Thr Thr Asn Phe Ser Glu Arg Tyr Ser Glu Glu
        1140                1145                1150

Glu Gln Gln Glu Asp Glu Thr Glu Arg Gln Asn Lys Tyr Asn Ile Lys
    1155                1160                1165

Ala Tyr Ala Ser Glu Glu His His Gly Glu Gln Pro Ile Asp Tyr Ser
1170                1175                1180

Arg Lys Tyr Ser Thr Asp Val Pro Ser Ser Ala Gln Lys Pro Ser Phe
1185                1190                1195                1200

Pro Tyr Ser Asn Asn Ser Ser Lys Gln Lys Pro Lys Lys Glu Gln Val
            1205                1210                1215

Ser Ser Asn Ser Asn Thr Pro Thr Pro Ser Pro Asn Ser Asn Arg Gln
        1220                1225                1230

Asn Gln Leu His Pro Asn Ser Ala Gln Ser Arg Pro Gly Leu Asn Arg
    1235                1240                1245

Pro Lys Gln Ile Pro Asn Lys Pro Pro Ser Ile Asn Gln Glu Thr Ile
1250                1255                1260

Gln Thr Tyr Cys Val Glu Asp Thr Pro Ile Cys Phe Ser Arg Gly Ser
1265                1270                1275                1280

Ser Leu Ser Ser Leu Ser Ser Ala Glu Asp Glu Ile Glu Gly Arg Glu
            1285                1290                1295

Arg Asn Ser Arg Gly Gln Glu Ser Asn Asn Thr Leu Gln Ile Thr Glu
        1300                1305                1310

Pro Lys Glu Ile Ser Ala Val Ser Lys Asp Gly Ala Val Asn Glu Thr
    1315                1320                1325

Arg Ser Ser Val His His Thr Arg Thr Lys Asn Asn Arg Leu Gln Thr
1330                1335                1340

Ser Asn Ile Ser Pro Ser Asp Ser Ser Arg His Lys Ser Val Glu Phe
1345                1350                1355                1360

Ser Ser Gly Ala Lys Ser Pro Ser Lys Ser Gly Ala Gln Thr Pro Lys
            1365                1370                1375

Ser Pro Pro Glu His Tyr Val Gln Glu Thr Pro Leu Met Phe Ser Arg
        1380                1385                1390

Cys Thr Ser Gly Ser Ser Leu Asp Ser Phe Glu Ser His Ser Ile Ala
    1395                1400                1405

Ser Ser Ile Ala Ser Ser Val Ala Ser Glu His Met Ile Ser Gly Ile
    1410                1415                1420

Ile Ser Pro Ser Asp Leu Pro Asp Ser Pro Gly Gln Thr Met Pro Pro
1425                1430                1435                1440

Ser Arg Ser Lys Thr Pro Pro Pro Gln Thr Val Gln Ala Lys Lys
            1445                1450                1455

Asp Gly Ser Lys Pro Ile Val Pro Asp Glu Arg Gly Lys Val Ala
        1460                1465                1470

Lys Thr Ala Val His Ser Ala Ile Gln Arg Val Gln Val Leu Gln Glu
    1475                1480                1485

Ala Asp Thr Leu Leu His Phe Ala Thr Glu Ser Thr Pro Asp Gly Phe
1490                1495                1500

Ser Cys Ala Ser Ser Leu Ser Ala Leu Ser Leu Asp Glu Pro Tyr Ile
1505                1510                1515                1520

Gln Lys Asp Val Gln Leu Lys Ile Met Pro Pro Val Leu Glu Asn Asp
            1525                1530                1535
```

```
Gln Gly Asn Lys Ala Glu Pro Glu Lys Glu Phe Ile Asp Asn Lys Ala
            1540                1545                1550

Lys Lys Glu Asp Lys Arg Ser Glu Gln Glu Lys Asp Met Leu Asp Asp
        1555                1560                1565

Thr Asp Asp Ile Asp Ile Leu Glu Glu Cys Ile Ile Ser Ala Met
    1570                1575                1580

Pro Arg Lys Pro Ser Arg Lys Asn Lys Lys Val Pro Gln Pro Thr Pro
1585                1590                1595                1600

Gly Lys Pro Pro Pro Val Ala Arg Lys Pro Ser Gln Leu Pro Val
                1605                1610                1615

Tyr Lys Leu Leu Ser Ser Gln Asn Arg Leu Gln Thr Gln Lys His Val
                1620                1625                1630

Asn Phe Thr His Ser Asp Asp Met Pro Arg Val Tyr Cys Val Glu Gly
            1635                1640                1645

Thr Pro Ile Asn Phe Ser Thr Ala Thr Ser Leu Ser Asp Leu Thr Ile
    1650                1655                1660

Glu Ser Pro Pro Ser Glu Pro Thr Asn Asp Gln Pro Asn Thr Asp Ser
1665                1670                1675                1680

Leu Ser Thr Asp Leu Glu Lys Arg Asp Thr Ile Pro Thr Glu Gly Arg
                1685                1690                1695

Ser Thr Asp Asp Thr Asp Ala Ser Lys Pro Leu Asn Pro Thr Thr Val
                1700                1705                1710

Leu Asp Glu Asp Lys Ala Glu Glu Gly Asp Ile Leu Ala Glu Cys Ile
            1715                1720                1725

His Ser Ala Met Pro Lys Gly Lys Ser His Lys Pro Tyr Arg Val Lys
    1730                1735                1740

Lys Ile Met Asp Gln Ile Asn His Thr Ser Ala Ala Thr Ser Ser Gly
1745                1750                1755                1760

Asn Ser Arg Ser Met Gln Glu Thr Asp Lys Asn Lys Pro Thr Ser Pro
                1765                1770                1775

Val Lys Pro Met Pro Gln Ser Ile Gly Phe Lys Glu Arg Leu Lys Lys
                1780                1785                1790

Asn Thr Glu Leu Lys Leu Asn Pro Asn Ser Glu Asn Gln Tyr Cys Asp
            1795                1800                1805

Pro Arg Lys Pro Ser Ser Lys Lys Pro Ser Lys Val Ala Asn Glu Lys
    1810                1815                1820

Ile Pro Asn Asn Glu Glu Arg Thr Lys Gly Phe Ala Phe Asp Ser Pro
1825                1830                1835                1840

His His Tyr Thr Pro Ile Glu Gly Thr Pro Tyr Cys Phe Ser Arg Asn
                1845                1850                1855

Asp Ser Leu Ser Ser Leu Asp Phe Glu Asp Asp Ile Asp Leu Ser
                1860                1865                1870

Lys Glu Lys Ala Glu Leu Arg Lys Glu Lys Gly Thr Lys Asp Thr Asp
            1875                1880                1885

Gln Lys Val Lys Tyr Lys His Glu Asn Arg Ala Ile Asn Pro Met Gly
    1890                1895                1900

Lys Gln Asp Gln Thr Gly Pro Lys Ser Leu Gly Gly Arg Asp Gln Pro
1905                1910                1915                1920

Lys Ala Leu Val Gln Lys Pro Thr Ser Phe Ser Ser Ala Ala Lys Gly
                1925                1930                1935

Thr Gln Asp Arg Gly Gly Ala Thr Asp Glu Lys Met Glu Asn Phe Ala
                1940                1945                1950

Ile Glu Asn Thr Pro Val Cys Phe Ser Arg Asn Ser Ser Leu Ser Ser
```

-continued

Leu Ser Asp Ile Asp Gln Glu Asn Asn Lys Glu Thr Glu Pro Leu
        1970            1975            1980

Lys Gln Thr Gly Thr Ser Glu Thr Gln Leu Gly Leu Arg Arg Pro Gln
1985            1990            1995            2000

Thr Ser Gly Tyr Ala Pro Lys Ser Phe His Val Glu Asp Thr Pro Val
        2005            2010            2015

Cys Phe Ser Arg Asn Ser Ser Leu Ser Ser Leu Ser Ile Asp Ser Glu
        2020            2025            2030

Asp Asp Leu Leu Gln Glu Cys Ile Ser Ser Ala Met Pro Lys Lys Arg
        2035            2040            2045

Lys Pro Ser Lys Ile Lys Asn Glu Val Gly Lys Ser Arg Ser Asn Ser
        2050            2055            2060

Val Gly Gly Ile Leu Ala Glu Glu Pro Asp Leu Thr Leu Asp Leu Arg
2065            2070            2075            2080

Asp Ile Gln Ser Pro Asp Ser Glu Asn Ala Phe Ser Pro Asp Ser Glu
        2085            2090            2095

Asn Phe Asp Trp Lys Ala Ile Gln Glu Gly Ala Asn Ser Ile Val Ser
        2100            2105            2110

Arg Leu His Gln Ala Ala Ala Ala Gly Ser Leu Ser Arg Gln Gly Ser
        2115            2120            2125

Ser Asp Ser Asp Ser Ile Leu Ser Leu Lys Ser Gly Ile Ser Leu Gly
        2130            2135            2140

Ser Pro Phe His Leu Thr Leu Asp Lys Glu Glu Lys Thr Ile Thr Ser
2145            2150            2155            2160

Asn Lys Gly Pro Lys Ile Leu Lys Pro Ala Glu Lys Ser Ala Leu Glu
        2165            2170            2175

Asn Lys Lys Thr Glu Glu Pro Lys Gly Ile Lys Gly Leu Lys Lys
        2180            2185            2190

Val Tyr Lys Ser Leu Ile Thr Gly Lys Ser Arg Ser Ser Ser Asp Phe
        2195            2200            2205

Ser Ser His Cys Lys Gln Ser Val Gln Thr Asn Met Pro Ser Ile Ser
        2210            2215            2220

Arg Gly Arg Thr Met Ile His Ile Pro Gly Val Arg Ala Ser Ser Pro
2225            2230            2235            2240

Ser Thr Ser Pro Val Ser Lys Lys Gly Pro Val Phe Lys Asn Val Pro
        2245            2250            2255

Ser Lys Gly Ser Asn Glu Asn Pro Ser Ser Ser Ser Pro Lys Gly
        2260            2265            2270

Thr Lys Pro Leu Lys Ser Glu Leu Val Tyr Gly Ser Arg Pro Ser Ser
        2275            2280            2285

Thr Pro Gly Gly Ser Ser Lys Gly Asn Ser Arg Ser Gly Ser Arg Asp
        2290            2295            2300

Ser Ala Ser Ser Arg Pro Ser Pro Gln Pro Leu Ser Arg Pro Leu Gln
2305            2310            2315            2320

Ser Pro Gly Arg Asn Ser Ile Ser Pro Gly Lys Asn Gly Ile Ser Pro
        2325            2330            2335

Pro Asn Lys Phe Ser Gln Leu Pro Arg Thr Thr Ser Pro Ser Thr Ala
        2340            2345            2350

Ser Thr Lys Ser Ser Gly Ser Gly Arg Met Ser Tyr Thr Ser Pro Gly
        2355            2360            2365

Arg Gln Leu Ser Gln Pro Asn Leu Ser Lys Gln Ser Gly Leu Pro Lys
        2370            2375            2380

```
Thr His Ser Ser Ile Pro Arg Ser Glu Ser Ala Ser Lys Ser Leu Asn
2385                2390                2395                2400

Gln Asn Val Asn Thr Gly Ser Asn Lys Lys Val Glu Leu Ser Arg Met
            2405                2410                2415

Ser Ser Thr Lys Ser Ser Gly Ser Glu Ser Asp Arg Ser Glu Arg Pro
        2420                2425                2430

Ala Leu Val Arg Gln Ser Thr Phe Ile Lys Glu Ala Pro Ser Pro Thr
    2435                2440                2445

Leu Arg Arg Lys Leu Glu Glu Ser Ala Ser Phe Glu Ser Leu Ser Ser
2450                2455                2460

Ser Ser Arg Ala Asp Ser Pro Arg Ser Gln Thr Gln Thr Pro Ala
2465                2470                2475                2480

Leu Ser Pro Ser Leu Pro Asp Met Ala Leu Ser Thr His Ser Ile Gln
                2485                2490                2495

Ala Gly Gly Trp Arg Lys Met Pro Pro Asn Leu Asn Pro Ala Ala Glu
            2500                2505                2510

His Gly Asp Ser Arg Arg Arg His Asp Ile Ser Arg Ser His Ser Glu
        2515                2520                2525

Ser Pro Ser Arg Leu Pro Ile Thr Arg Ser Gly Thr Trp Lys Arg Glu
    2530                2535                2540

His Ser Lys His Ser Ser Ser Leu Pro Arg Val Ser Thr Trp Arg Arg
2545                2550                2555                2560

Thr Gly Ser Ser Ser Ser Ile Leu Ser Ala Ser Ser Glu Ser Ser Glu
                2565                2570                2575

Lys Ala Lys Ser Glu Asp Glu Lys Gln Gln Val Cys Ser Phe Pro Gly
            2580                2585                2590

Pro Arg Ser Glu Cys Ser Ser Ala Lys Gly Thr Trp Arg Lys Ile
        2595                2600                2605

Lys Glu Ser Glu Ile Leu Glu Thr Pro Ser Asn Gly Ser Ser Ser Thr
    2610                2615                2620

Ile Ala Glu Ser Asn Cys Ser Leu Glu Ser Lys Thr Leu Val Tyr Gln
2625                2630                2635                2640

Met Ala Pro Ala Val Ser Lys Thr Glu Asp Val Trp Val Arg Ile Glu
                2645                2650                2655

Asp Cys Pro Ile Asn Asn Pro Arg Ser Gly Arg Ser Pro Thr Gly Asn
            2660                2665                2670

Ser Pro Pro Val Ile Asp Asn Val Leu Asp Gln Gly Gln Lys Glu Glu
        2675                2680                2685

Ala Ala Lys Asp Cys His Thr Arg His Asn Ser Gly Asn Gly Asn Val
    2690                2695                2700

Pro Leu Leu Glu Asn Arg Gln Lys Ser Phe Ile Lys Val Asp Gly Leu
2705                2710                2715                2720

Asp Thr Lys Gly Thr Asp Pro Lys Ser Leu Ile Asn Asn Gln Gln Glu
                2725                2730                2735

Thr Asn Glu Asn Thr Val Ala Glu Arg Thr Ala Phe Ser Ser Ser Ser
            2740                2745                2750

Ser Ser Lys His Ser Ser Pro Ser Gly Thr Val Ala Ala Arg Val Thr
        2755                2760                2765

Pro Phe Asn Tyr Asn Pro Ser Pro Arg Lys Ser Asn Gly Glu Asn Ser
    2770                2775                2780

Thr Ser Arg Pro Ser Gln Ile Pro Thr Pro Val Thr Asn Ser Thr Lys
2785                2790                2795                2800

Lys Arg Asp Ser Lys Thr Glu Thr Thr Asp Ser Ser Gly Ser Gln Ser
                2805                2810                2815
```

Pro Lys Arg His Ser Gly Ser Tyr Leu Val Thr Ser Val
         2820                2825

<210> SEQ ID NO 2
<211> LENGTH: 30
<212> TYPE: DNA
<213> ORGANISM: Artificial Sequence
<220> FEATURE:
<223> OTHER INFORMATION: Aritifically synthesized primer sequence

<400> SEQUENCE: 2
cgacgcgtaa tgcattttct ccagactctg                                30

<210> SEQ ID NO 3
<211> LENGTH: 39
<212> TYPE: DNA
<213> ORGANISM: Artificial Sequence
<220> FEATURE:
<223> OTHER INFORMATION: Aritifically synthesized primer sequence

<400> SEQUENCE: 3
ggaattcgga tcctcacacc agataagaac cagagtgcc                      39

<210> SEQ ID NO 4
<211> LENGTH: 33
<212> TYPE: DNA
<213> ORGANISM: Artificial Sequence
<220> FEATURE:
<223> OTHER INFORMATION: Aritifically synthesized primer sequence

<400> SEQUENCE: 4
cgacgcgtat ggctgctgct tcgtatgatc agt                            33

<210> SEQ ID NO 5
<211> LENGTH: 29
<212> TYPE: DNA
<213> ORGANISM: Artificial Sequence
<220> FEATURE:
<223> OTHER INFORMATION: Aritifically synthesized primer sequence

<400> SEQUENCE: 5
cgacgcgtac ctgctgttct ttccctgtc                                 29

<210> SEQ ID NO 6
<211> LENGTH: 28
<212> TYPE: DNA
<213> ORGANISM: Artificial Sequence
<220> FEATURE:
<223> OTHER INFORMATION: Aritifically synthesized primer sequence

<400> SEQUENCE: 6
ctagctagca tggctgctgc ttcgtatg                                  28

<210> SEQ ID NO 7
<211> LENGTH: 27
<212> TYPE: DNA
<213> ORGANISM: Artificial Sequence
<220> FEATURE:
<223> OTHER INFORMATION: Aritifically synthesized primer sequence

<400> SEQUENCE: 7
cctgtcccaa gtaggtcacg atcgatc                                   27

<210> SEQ ID NO 8
<211> LENGTH: 27
<212> TYPE: DNA

```
<213> ORGANISM: Artificial Sequence
<220> FEATURE:
<223> OTHER INFORMATION: Aritifically synthesized primer sequence

<400> SEQUENCE: 8
ctagctagcc tcggcaacta ccattcg                                          27

<210> SEQ ID NO 9
<211> LENGTH: 19
<212> TYPE: DNA
<213> ORGANISM: Artificial Sequence
<220> FEATURE:
<223> OTHER INFORMATION: Aritifically synthesized primer sequence

<400> SEQUENCE: 9
attagagctc actctagac                                                   19
```